(12) United States Patent
Miller

(10) Patent No.: US 12,256,893 B2
(45) Date of Patent: Mar. 25, 2025

(54) ENDOSCOPE ACCESSORY AND MEDICAL DEVICE KIT

(71) Applicant: GI Scientific, LLC, Arlington, VA (US)

(72) Inventor: Scott Miller, Arlington, VA (US)

( * ) Notice: Subject to any disclaimer, the term of this patent is extended or adjusted under 35 U.S.C. 154(b) by 10 days.

(21) Appl. No.: 16/717,804

(22) Filed: Dec. 17, 2019

(65) Prior Publication Data
US 2020/0178767 A1 Jun. 11, 2020

Related U.S. Application Data

(63) Continuation-in-part of application No. PCT/US2016/043371, filed on Jul. 21, 2016.
(Continued)

(51) Int. Cl.
*A61B 1/00* (2006.01)
*A61B 1/01* (2006.01)
(Continued)

(52) U.S. Cl.
CPC ...... *A61B 1/00098* (2013.01); *A61B 1/00089* (2013.01); *A61B 1/00096* (2013.01);
(Continued)

(58) Field of Classification Search
CPC ............ A61B 1/00098; A61B 1/00089; A61B 1/0676; A61B 1/00137; A61B 1/00101;
(Continued)

(56) References Cited

U.S. PATENT DOCUMENTS

| 3,774,614 A | 11/1973 | Cook |
| 3,858,577 A | 1/1975 | Bass et al. |

(Continued)

FOREIGN PATENT DOCUMENTS

| CA | 2863587 A1 * | 8/2012 | ......... A61B 1/00066 |
| CN | 1692872 A | 11/2011 | |

(Continued)

OTHER PUBLICATIONS

Republic of China Patent Office; Office Action; Chinese Patent Application No. 201680054885.0; Jun. 3, 2020.
(Continued)

*Primary Examiner* — Aaron B Fairchild
*Assistant Examiner* — Stephen Floyd London
(74) *Attorney, Agent, or Firm* — Farber LLC

(57) ABSTRACT

A coupler device for a forward viewing endoscope comprises a main body having a proximal end configured to attach to the distal end portion of the endoscope and a distal end portion that at least partially seals the distal end portion of the scope and allows for viewing of the surgical site. The coupler device may include a flexible working channel extension for attachment to the working channel of the endoscope. The coupler device provides a protective cover to reduce the ingress of debris, fluid, bacteria, or other unwanted matter from the working end of the endoscope which could lead to infection and decreased performance of the scope. A kit for use in an endoscopic procedure on a patient comprises the coupler device and an end viewing endoscope having a working channel, a light and a camera lens.

19 Claims, 19 Drawing Sheets

Related U.S. Application Data

(60) Provisional application No. 62/195,291, filed on Jul. 21, 2015.

(51) Int. Cl.
- *A61B 1/015* (2006.01)
- *A61B 1/018* (2006.01)
- *A61B 1/06* (2006.01)
- *A61B 1/12* (2006.01)
- *A61B 1/273* (2006.01)

(52) U.S. Cl.
CPC ...... *A61B 1/00101* (2013.01); *A61B 1/00105* (2013.01); *A61B 1/00131* (2013.01); *A61B 1/00133* (2013.01); *A61B 1/00137* (2013.01); *A61B 1/00142* (2013.01); *A61B 1/00165* (2013.01); *A61B 1/00177* (2013.01); *A61B 1/01* (2013.01); *A61B 1/015* (2013.01); *A61B 1/018* (2013.01); *A61B 1/0676* (2013.01); *A61B 1/126* (2013.01); *A61B 1/2736* (2013.01); *A61B 1/00103* (2013.01); *A61B 1/00181* (2013.01)

(58) Field of Classification Search
CPC ... A61B 1/00133; A61B 1/01; A61B 1/00105; A61B 1/00096; A61B 1/00131; A61B 1/00142; A61B 1/00165; A61B 1/015; A61B 1/018; A61B 1/126; A61B 1/2736; A61B 1/00177; A61B 1/00181; A61B 1/00103; A61B 1/005; A61B 1/012; A61B 1/00087; A61B 1/00091; A61B 1/00094; A61B 1/00119; A61B 1/00128; A61B 1/00135; A61B 1/0125

USPC ...................................................... 600/175

See application file for complete search history.

(56) References Cited

U.S. PATENT DOCUMENTS

| | | |
|---|---|---|
| 4,090,501 A | 5/1978 | Chaitin |
| 4,201,199 A | 5/1980 | Smith |
| 4,207,872 A | 6/1980 | Meiri et al. |
| 4,340,811 A | 7/1982 | Yamashita et al. |
| 4,436,087 A * | 3/1984 | Ouchi ............ A61M 25/0133 600/153 |
| 4,681,093 A | 7/1987 | Ono et al. |
| 4,696,544 A | 9/1987 | Costella |
| 4,744,620 A | 5/1988 | Ueno et al. |
| 4,779,611 A | 10/1988 | Grooters et al. |
| 4,805,598 A | 2/1989 | Ueda |
| 4,878,725 A | 11/1989 | Hessel et al. |
| 4,881,810 A | 11/1989 | Hasegawa |
| 4,888,243 A | 12/1989 | Jonas et al. |
| 4,949,706 A * | 8/1990 | Thon ............... A61B 1/00135 600/107 |
| 4,967,732 A | 11/1990 | Inoue |
| 5,040,715 A | 8/1991 | Green et al. |
| 5,050,585 A | 9/1991 | Takahashi |
| 5,080,660 A | 1/1992 | Buelna |
| 5,104,025 A | 4/1992 | Main et al. |
| 5,137,198 A | 8/1992 | Nobis et al. |
| 5,201,900 A | 4/1993 | Nardella |
| 5,205,459 A | 4/1993 | Brinkerhoff et al. |
| 5,237,984 A | 8/1993 | Williams, III et al. |
| 5,271,379 A | 12/1993 | Phan et al. |
| 5,326,013 A | 7/1994 | Green et al. |
| 5,329,935 A | 7/1994 | Takahashi |
| 5,337,734 A | 8/1994 | Saab |
| 5,342,388 A | 8/1994 | Toller |
| 5,413,052 A | 5/1995 | Breezer et al. |
| 5,413,268 A | 5/1995 | Green et al. |
| 5,443,781 A | 8/1995 | Saab |
| 5,448,990 A | 9/1995 | De Faria-Correa |
| 5,460,168 A | 10/1995 | Masubuchi et al. |
| 5,476,206 A | 12/1995 | Green et al. |
| 5,536,236 A | 7/1996 | Yabe et al. |
| 5,555,129 A | 9/1996 | Konno et al. |
| 5,569,157 A * | 10/1996 | Nakazawa ......... A61B 1/0008 600/104 |
| 5,575,291 A | 11/1996 | Hayakawa et al. |
| 5,605,532 A | 2/1997 | Schermerhorn |
| 5,632,717 A | 5/1997 | Yoon |
| 5,657,921 A | 8/1997 | Young et al. |
| 5,662,258 A | 9/1997 | Knodel et al. |
| 5,674,181 A | 10/1997 | Iida |
| 5,707,342 A | 1/1998 | Tanaka |
| 5,725,474 A | 3/1998 | Yasui et al. |
| 5,725,475 A | 3/1998 | Yasui et al. |
| 5,738,629 A | 4/1998 | Moll et al. |
| 5,743,851 A | 4/1998 | Moll et al. |
| 5,771,327 A | 6/1998 | Bar-Or et al. |
| 5,788,628 A | 8/1998 | Matsuno et al. |
| 5,808,813 A | 9/1998 | Lucey et al. |
| 5,840,014 A | 11/1998 | Miyano et al. |
| 5,860,913 A | 1/1999 | Yamaya et al. |
| 5,897,487 A | 4/1999 | Ouchi |
| 5,916,148 A | 6/1999 | Tsuyuki |
| 6,059,719 A | 5/2000 | Yamamoto et al. |
| 6,131,789 A | 10/2000 | Schulze et al. |
| 6,217,509 B1 | 4/2001 | Foley et al. |
| 6,250,532 B1 | 6/2001 | Green et al. |
| 6,277,065 B1 | 8/2001 | Donofrio |
| 6,283,951 B1 | 9/2001 | Flaherty et al. |
| 6,293,907 B1 | 9/2001 | Axon et al. |
| 6,306,081 B1 | 10/2001 | Ishikawa et al. |
| 6,409,725 B1 | 6/2002 | Khandkar et al. |
| 6,416,462 B1 | 7/2002 | Tovey et al. |
| 6,458,074 B1 * | 10/2002 | Matsui .................. A61B 1/018 600/106 |
| 6,673,091 B1 | 1/2004 | Shaffer et al. |
| 6,689,130 B2 | 2/2004 | Arai et al. |
| 6,699,180 B2 | 3/2004 | Kobayashi |
| 6,712,524 B2 | 3/2004 | Beatty et al. |
| 6,723,350 B2 | 4/2004 | Burrell et al. |
| 6,733,440 B2 | 5/2004 | Ailinger et al. |
| 6,770,069 B1 | 8/2004 | Hobart et al. |
| 6,792,837 B2 | 9/2004 | Battistone |
| 6,855,108 B2 | 2/2005 | Ishibiki et al. |
| 6,866,627 B2 | 3/2005 | Nozue |
| 6,934,093 B2 | 8/2005 | Kislev et al. |
| 6,981,628 B2 | 1/2006 | Wales |
| 6,988,650 B2 | 1/2006 | Schwemberger et al. |
| 7,033,317 B2 | 4/2006 | Pruitt |
| 7,046,439 B2 | 5/2006 | Kaminsky et al. |
| 7,087,012 B2 | 8/2006 | Ishibiki |
| 7,112,195 B2 | 9/2006 | Boll et al. |
| 7,205,339 B2 | 4/2007 | Muratoglu |
| 7,235,592 B2 | 6/2007 | Muratoglu et al. |
| 7,238,153 B2 | 7/2007 | Moriyama |
| 7,245,813 B2 | 7/2007 | Brown et al. |
| 7,464,847 B2 | 12/2008 | Viola et al. |
| 7,537,561 B2 | 5/2009 | Yamaya et al. |
| 7,553,278 B2 | 6/2009 | Kucklick |
| 7,554,743 B2 | 6/2009 | Jiang et al. |
| 7,566,993 B2 | 7/2009 | May |
| 7,621,868 B2 | 11/2009 | Breidenthal et al. |
| 7,819,872 B2 | 10/2010 | Johnson et al. |
| 7,977,255 B1 | 7/2011 | Scheer et al. |
| 8,180,423 B2 | 5/2012 | Mang et al. |
| 8,905,921 B2 | 12/2014 | Titus |
| 8,915,931 B2 | 12/2014 | Boudreaux et al. |
| 9,459,442 B2 | 10/2016 | Miller |
| 9,709,795 B2 | 7/2017 | Miller |
| 10,101,574 B2 | 10/2018 | Miller |
| 2002/0035311 A1 | 3/2002 | Ouchi |
| 2002/0065515 A1 | 5/2002 | Falwell et al. |
| 2002/0133148 A1 | 9/2002 | Daniel et al. |
| 2003/0040657 A1 | 2/2003 | Yamaya et al. |
| 2003/0181900 A1 | 9/2003 | Long |
| 2004/0077927 A1 * | 4/2004 | Ouchi .................. A61B 1/018 600/123 |

(56) References Cited

U.S. PATENT DOCUMENTS

| | | | |
|---|---|---|---|
| 2004/0106850 A1* | 6/2004 | Yamaya | A61B 1/00098 600/107 |
| 2004/0157073 A1 | 8/2004 | Burrell et al. | |
| 2004/0249246 A1 | 12/2004 | Campos | |
| 2004/0263613 A1 | 12/2004 | Morita | |
| 2004/0267092 A1 | 12/2004 | Ishibiki | |
| 2005/0043589 A1 | 2/2005 | Pruitt | |
| 2005/0080411 A1 | 4/2005 | Ouchi | |
| 2005/0131279 A1 | 6/2005 | Boulais et al. | |
| 2005/0197530 A1 | 9/2005 | Wallace et al. | |
| 2005/0234297 A1* | 10/2005 | Devierre | A61B 1/00087 600/129 |
| 2006/0030844 A1 | 2/2006 | Knight et al. | |
| 2006/0084839 A1 | 4/2006 | Mourlas et al. | |
| 2006/0173241 A1 | 8/2006 | Ouchi et al. | |
| 2006/0200176 A1 | 9/2006 | Matsuno et al. | |
| 2006/0229662 A1 | 10/2006 | Finkielsztein et al. | |
| 2006/0235271 A1* | 10/2006 | Carter | A61B 1/018 600/107 |
| 2006/0270900 A1 | 11/2006 | Chin et al. | |
| 2006/0270978 A1 | 11/2006 | Binmoeller | |
| 2006/0287572 A1* | 12/2006 | Wimmer | A61B 1/018 600/129 |
| 2007/0038043 A1 | 2/2007 | Gelikonov et al. | |
| 2007/0066869 A1 | 3/2007 | Hoffman | |
| 2007/0066870 A1 | 3/2007 | Ohashi et al. | |
| 2007/0073108 A1 | 3/2007 | Takahashi | |
| 2007/0099500 A1* | 5/2007 | Pilvisto | A61B 1/00098 439/584 |
| 2007/0208219 A1 | 9/2007 | Carter | |
| 2007/0239620 A1 | 10/2007 | Schwartz et al. | |
| 2007/0260117 A1 | 11/2007 | Zwolinski et al. | |
| 2007/0270897 A1 | 11/2007 | Skerven | |
| 2007/0282256 A1 | 12/2007 | Hu et al. | |
| 2007/0293888 A1 | 12/2007 | Harren et al. | |
| 2008/0021268 A1 | 1/2008 | Shoroji et al. | |
| 2008/0021269 A1 | 1/2008 | Tinkham et al. | |
| 2008/0033246 A1 | 2/2008 | Matsui et al. | |
| 2008/0139885 A1 | 6/2008 | Knapp | |
| 2008/0188874 A1 | 8/2008 | Henderson | |
| 2008/0262295 A1 | 10/2008 | Kendale et al. | |
| 2008/0306335 A1 | 12/2008 | Lau et al. | |
| 2009/0048483 A1 | 2/2009 | Yamamoto | |
| 2009/0048486 A1 | 2/2009 | Surti | |
| 2009/0062790 A1 | 3/2009 | Malchano et al. | |
| 2009/0098409 A1 | 4/2009 | Yamada et al. | |
| 2009/0124858 A1 | 5/2009 | Oskin et al. | |
| 2009/0143643 A1 | 6/2009 | Weitzner et al. | |
| 2009/0156898 A1 | 6/2009 | Ichimura | |
| 2009/0254164 A1 | 10/2009 | Johnson et al. | |
| 2009/0315989 A1 | 12/2009 | Adelson | |
| 2009/0326328 A1 | 12/2009 | Kucklick | |
| 2010/0026940 A1 | 2/2010 | Takegami et al. | |
| 2010/0121442 A1 | 5/2010 | Shea et al. | |
| 2010/0017414 A1 | 7/2010 | Hsu | |
| 2010/0203454 A1 | 8/2010 | Brongersma et al. | |
| 2010/0268027 A1 | 10/2010 | Aono et al. | |
| 2010/0286475 A1 | 11/2010 | Robertson | |
| 2011/0065985 A1* | 3/2011 | Wehrheim | A61B 1/018 600/106 |
| 2011/0124960 A1 | 5/2011 | St. Onge et al. | |
| 2011/0152610 A1* | 6/2011 | Trusty | A61B 1/00096 600/104 |
| 2011/0152618 A1 | 6/2011 | Surti | |
| 2011/0190578 A1* | 8/2011 | Ho | A61B 1/00087 600/104 |
| 2011/0241460 A1 | 10/2011 | Jiang | |
| 2012/0034573 A1 | 2/2012 | Erdmann et al. | |
| 2012/0209074 A1* | 8/2012 | Titus | A61B 1/00137 600/153 |
| 2012/0209090 A1 | 8/2012 | Goodall et al. | |
| 2012/0232342 A1 | 9/2012 | Reydel | |
| 2013/0040516 A1 | 2/2013 | Pruneri et al. | |
| 2013/0090527 A1 | 4/2013 | Axon | |
| 2013/0144287 A1 | 6/2013 | Crowley et al. | |
| 2013/0190562 A1 | 7/2013 | Smith et al. | |
| 2013/0237998 A1 | 9/2013 | Wallace et al. | |
| 2014/0027578 A1 | 1/2014 | Comtesse | |
| 2015/0065795 A1 | 3/2015 | Titus | |
| 2015/0073214 A1 | 3/2015 | Ueda | |
| 2015/0351776 A1* | 12/2015 | Swayze | A61B 17/00491 600/104 |
| 2016/0051135 A1 | 2/2016 | Greenberg et al. | |
| 2016/0270636 A1 | 9/2016 | Iwasaka et al. | |
| 2017/0066111 A1 | 3/2017 | Wang | |
| 2017/0224198 A1* | 8/2017 | Yanagihara | A61B 1/0057 |
| 2017/0251908 A1* | 9/2017 | Surti | A61B 1/0684 |
| 2017/0251910 A1 | 9/2017 | Surti et al. | |
| 2017/0311789 A1 | 11/2017 | Mulcahey et al. | |
| 2017/0311974 A1 | 11/2017 | Friedrichs | |
| 2017/0325666 A1* | 11/2017 | Jiang | A61B 17/29 |
| 2018/0160886 A1 | 6/2018 | Govani et al. | |
| 2018/0206708 A1* | 7/2018 | Miller | A61B 1/00177 |
| 2019/0009963 A1 | 1/2019 | Wessely | |
| 2019/0070998 A1 | 3/2019 | Spencer et al. | |
| 2020/0100655 A1 | 4/2020 | Morishima et al. | |
| 2021/0015348 A1* | 1/2021 | Wilder | A61B 1/0057 |

FOREIGN PATENT DOCUMENTS

| | | | |
|---|---|---|---|
| DE | 3532609 | A | 3/1987 |
| EP | 1870018 | A2 | 12/2007 |
| JP | H0373168 | A | 3/1991 |
| JP | 07-178094 | A | 7/1995 |
| JP | 09238893 | A * | 9/1997 |
| JP | H09238893 | A | 9/1997 |
| JP | 05-123288 | A | 5/1999 |
| JP | 2000300570 | A | 10/2000 |
| JP | 3124079 | B2 | 1/2001 |
| JP | 200217655 | A | 1/2002 |
| JP | 2002233491 | A | 8/2002 |
| JP | 2003033319 | A | 2/2003 |
| JP | 2003339631 | A | 12/2003 |
| JP | 2005066139 | A | 3/2005 |
| JP | 2006026344 | A | 2/2006 |
| JP | 2008-029384 | A | 2/2008 |
| JP | 2009261830 | A | 11/2009 |
| JP | 2010063721 | A | 3/2010 |
| WO | WO 9929362 | A1 | 6/1999 |
| WO | WO 2001085319 | A1 | 11/2001 |
| WO | WO 2006138409 | A2 | 12/2006 |
| WO | WO 2007029230 | A2 | 3/2007 |
| WO | WO 2007029814 | A1 | 3/2007 |
| WO | WO 2007147060 | A2 | 12/2007 |
| WO | WO 2009149042 | A2 | 12/2009 |
| WO | WO 2011085319 | A1 | 7/2011 |
| WO | WO 2011099329 | A1 | 8/2011 |
| WO | WO 2011148172 | A2 | 12/2011 |
| WO | WO 2014123563 | A1 | 8/2014 |
| WO | WO 2017011535 | A1 | 1/2017 |

OTHER PUBLICATIONS

European Examination Report for EP Appl. No. 15843356.5 dated May 20, 2019, 7 pages.

Extended European Search Report for EP Appl. No. 16828548.4 dated Feb. 28, 2019.

Extended European Search Report for EP Appl. No. 16804476.6 dated Dec. 5, 2018.

Extended European Search Report and Written Opinion for EP Appl. No. 16804462-6 dated Dec. 10, 2018.

Extended European Search Report for EP Appl. No. 12747511.9 dated Jan. 3, 2018.

Extended European Search Report for EP Appl. No. 18174913.6 dated Aug. 16, 2019.

International Preliminary Report on Patentability issued in PCT/US2015/051662 dated Apr. 6, 2017.

International Search Report and Written Opinion for PCT Appl. No. PCT/US2019/012448 mailed Apr. 16, 2019.

(56) References Cited

OTHER PUBLICATIONS

International Search Report and Written Opinion dated Oct. 26, 2016 for PCT Application No. PCT/US2016/043371, filed Jul. 21, 2016.
International Search Report issued in corresponding International Application No. PCT/US2015/051662 dated Dec. 14, 2015.
International Search Report and Written Opinion dated Sep. 21, 2012 for PCT Appl. No. PCT/US2012/025404.
Japanese Patent Office, Notification of Reasons for Refusal, JP Appl. No. 2013-554596, Dec. 8, 2015.
Chinese Office Action and Search Report for CN Appl. No. 201280014363, Mar. 23, 2015.
Chinese Office Action for CN Appl. No. 201280014363, Jan. 5, 2016.
Chinese Office Action for CN Appl. No. 201680045602.6 dated Jun. 5, 2019.
First Examination Report for Indian Appl. No. 6566/CHENP/2013 dated Aug. 29, 2019.
Beneq Biocompatible Coatings Webpage.
Cargille Laboratories, Inc. Material Safety Data Sheet—Cargille Optical Gel Code 0607, Jun. 3, 2005.
Depth of Field, OPMI Application Tip #2, Informed for Medical Professionals in Neuro, ENT and Spine, 2nd Issue, Oct. 2006, Published by Carl Zeiss Surgical GmbH, Germany.
Jaxton, et al., An Experimental Investigation on the Development of Hydrogels for Optical Applications, Polymer Testing, 2003, 22(4):371-374, English Abstract.
Kopp, et al., Chapter 9, Optical Principles of the Endoscope, Hysteroscopy: Visual Perspectives of Uterine Anatomy, Physiology & Pathology, 3rd Edition, Lippincott Williams & Wilkins, 2007, 19 pages.
Maquet Training Manual, Vasoview 6 Endoscopic Vessel Harvesting System, Cardiovascular, Copyright Maquet Cardiovascular LLC, Oct. 2008.
Oil Immersion, From Wikipedia, http://en.wikipedia.org/wiki/Oil.sub.--immerson, Printed Sep. 7, 2010.
Olympus Colonoscopes Outpatient Doctor Surgery Center, http://outpatientsurgicare.com/index.PHP?Facilities:Technologies:Olympus.sub.--Colonoscopes&print, Printed Oct. 26, 2010.
Olympus Disposal Distal Attachment Product Data Sheet.
Olympus Evis Exera Colonovideoscope/Sigmoidovideoscope, Olympus CF Type Q1601JUS, Today's Most Versatile Choice for Colonoscopy, Product Data Sheet.
Olympus Technologies Evis Exera II, Learn About Wide—Angle, http://www.olympusamerica.com/msg.sub.--section/ msg.sub.--endoscopy.sub.---technology.asp, Copyright 2010 Olympus America Inc.
Olympus Technologies Evis Exera II, Learn About Close Focus, http://www.olympusamerica.com/msg.sub.--section/ msg.sub.--endoscopy.sub.---technology.asp, Copyright 2010 Olympus America Inc.
Olympus NA-11J-KB Product Data Sheet.
Optical Gels for Fiber-Optic Connectors and Splices—A Tutorial, Nye Optical Products, 6 pages.
Paxton, et al., An Experimental Investigation on the Development of Hydrogels for Optical Applications, Polymer Testing, 2003, 22(4):371-374, English Abstract.
Sigma-Aldrich Poly(2-hydroxyethyl methacrylate) Product Data Sheet, http://www.sigmaaldrich.com/catalog/Product Detail, Copyright 2010 Sigma-Aldrich Co.
Sigma-Aldrich Poly(ethylene glycol) Product Data Sheet, http://www.sigmaaldrich.com/catalog/Product Detail, Copyright 2010 Sigma-Aldrich Co.
Sigma-Aldrich Poly(vinyl alcohol) Product Data Sheet, http://www.sigmaaldrich.com/catalog/Product Detail, Copyright 2010 Sigma-Aldrich Co.
Sigma-Aldrich Methacrylic acid Product Data Sheet, http://www.sigmaaldrich.com/catalog/Product Detail, Printed Sep. 3, 2010.
SmartGel Nye Nyogel OCK-451LPH Product Data Sheet, Nye Optical Products.
Smeds, et al., Photocrosslinkable Polysaccharides for in situ Hydrogel Formation, Journal of Biomedical Materials Research, 2001, 54:115-121.
Stadler, Transparent conducting oxides—An up-to-date overview, Materials 5.4:661-683, 2012.
The Basics of Silicon Chemistry, Basic Silicon Production and Siloxane Polymerization, http://www.dowcorning.com/ content/sitech/sitechbasics/siloxane.sub.--poly-merization.asp, Copyright 2000-2010 Dow Corning Corporation.
Uw Eye Research Institute, Newsletter, Point of View, Summer 2009, http://vision.wisc.edu/news.sub.--sum09.html, Printed Feb. 5, 2010.
Vinyl Sustainability Forum 2014, Title: Benefits of PVC, Date retrieved: Mar. 7, 2014 from website: http://www.pvc.org/ en/p/benefits-of-pvc, pp. 1-4.
Zeng, et al., An Endoscope Utilizing Tunable-Focus Microlenses Actuated through Infrared Light, Solid-State Sensors, Actuators and Microsystems Conference, 2009, Transducers 2009, International, Issue 21-25, pp. 1214-1217, Abstract Only.
Zeng, et al., Tunable Liquid Microlens Actuated by Infrared Light-Responsive Hydrogel, Applied Physics Letters, 2008, 93:151101-1-151101-3.
International Search Report and Written Opinion dated Dec. 16, 2020 for PCT Appl. No. PCT/US2020/65429.
International Search Report and Written Opinion dated Dec. 16, 2020 for PCT Appl. No. PCT/US2020/65424.
International Search Report and Written Opinion dated Dec. 16, 2020 for PCT Appl. No. PCT/US2020/65427.
International Preliminary Report on Patentability; PCT/US2021/026528; GI Scientific, LLC; Oct. 20, 2022.

* cited by examiner

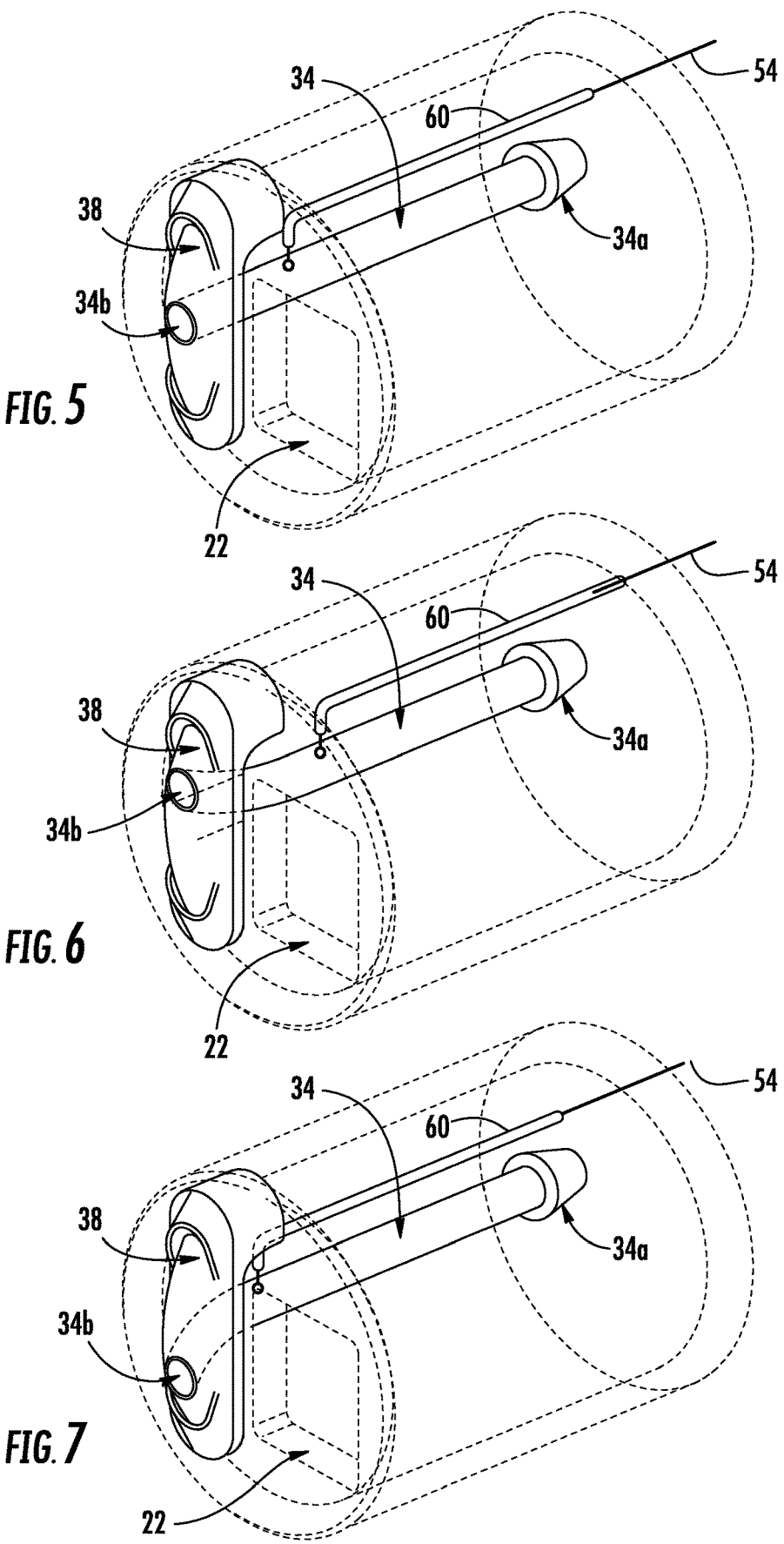

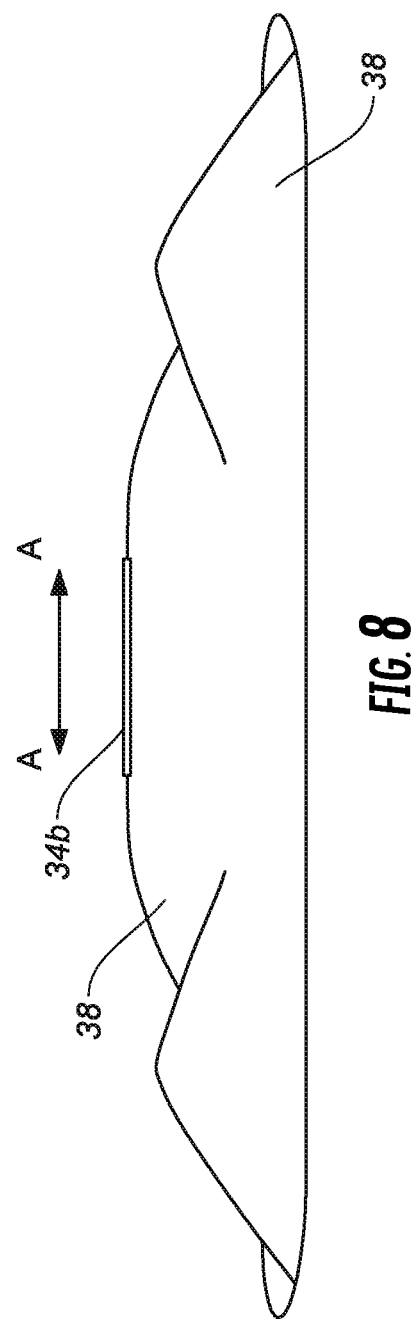

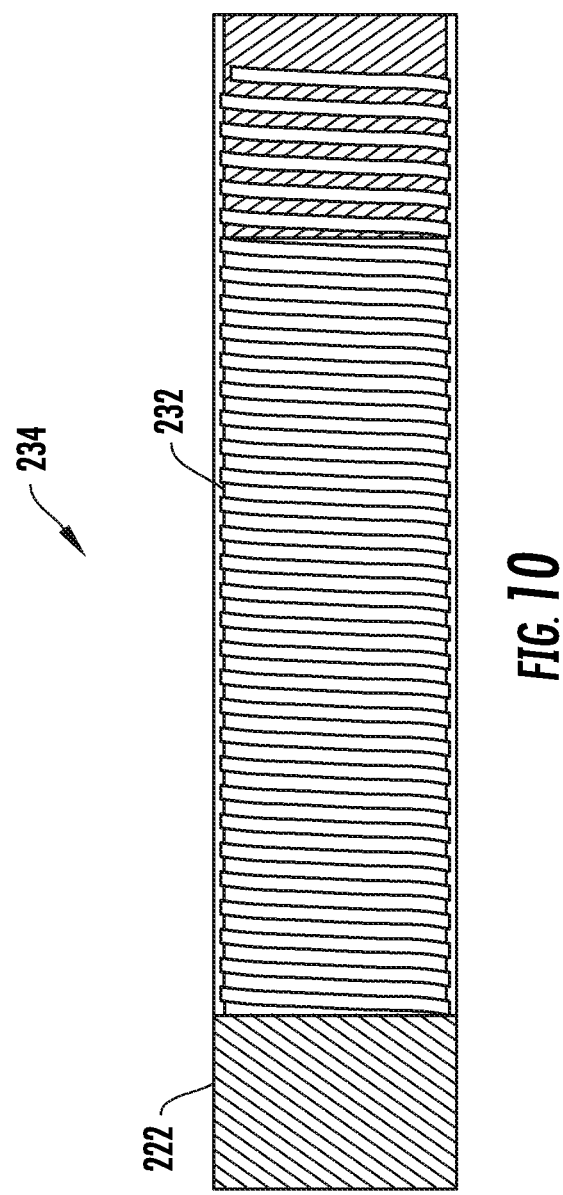

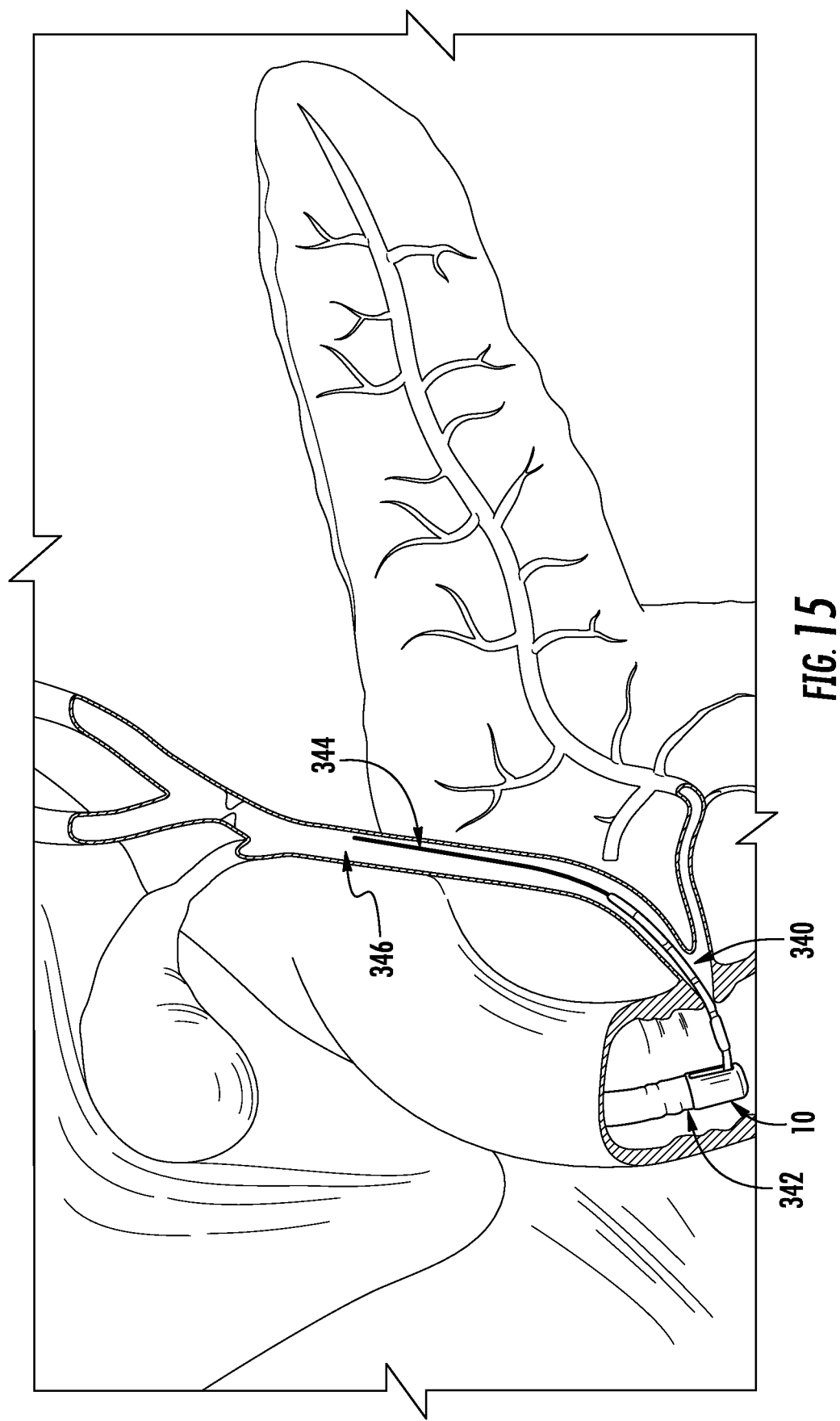

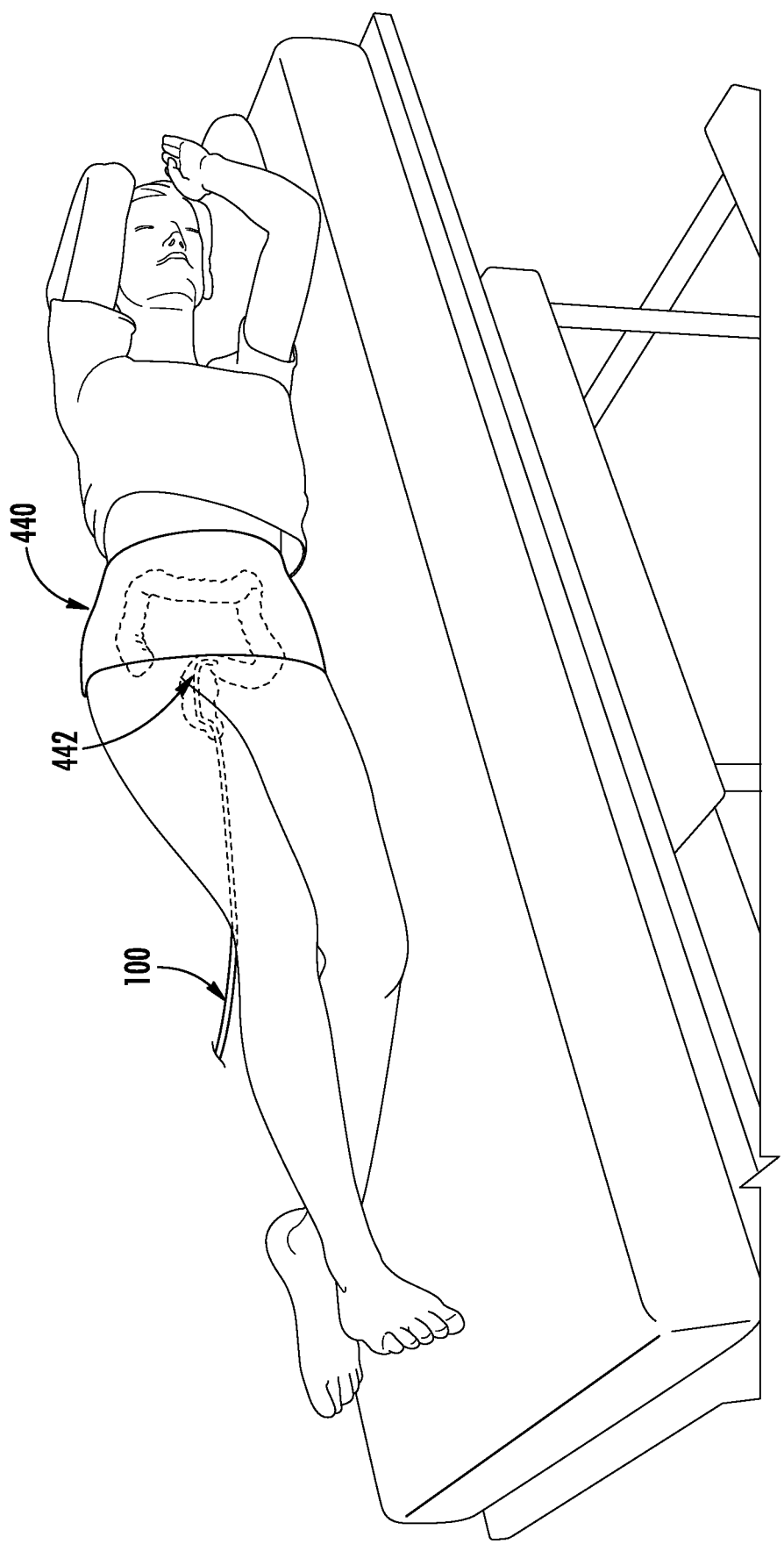

ENDOSCOPE ACCESSORY AND MEDICAL DEVICE KIT

CROSS-REFERENCE TO RELATED APPLICATIONS

This application is a continuation-in-part of PCT Patent Application No. PCT/US2016/043371, filed Jul. 21, 2016, which claims the benefit of U.S. Provisional Application No. 62/195,291, filed Jul. 21, 2015, the entire disclosures of which are incorporated herein by reference for all purposes.

FIELD

The present disclosure relates to coupler devices for covering and extending a working end portion of a forward viewing optical imaging endoscope and kits for use in an endoscope procedure that include the coupler device. The coupler device protects the working end portion from ingress of bacteria, tissue, fluid, and other debris which could lead to infection and decreased performance of the scope.

BACKGROUND

Recent advances in optical imaging technology have allowed many medical procedures to be performed today in a minimally invasive manner. The evolution of the more sophisticated, flexible scope with advanced visual capabilities has allowed access to regions deep within the human body that could only be achieved before with invasive surgical intervention. This modern day convenience has resulted in an increase in the demand for, as well as the number of, endoscopic, laparoscopic, arthroscopic, ophthalmoscopic, or other remote imaging visualization procedures performed every year in the U.S. and globally. While these procedures are relatively safe, they are not without risks.

Endoscopy, for instance, is a procedure in which a lighted visualization device called an endoscope is inserted into the patient's body to look inside a body cavity, lumen or organ, or combination, for the purpose of examination, diagnosis or treatment. The endoscope may be inserted through a small incision or through a natural opening of the patient. For example, in a bronchoscopy, the endoscope is inserted through the mouth, while in a sigmoidoscopy, the endoscope is inserted through the rectum, while in arthroscopy, the scope is inserted through a small incision . Unlike most other medical imaging devices, endoscopes are inserted directly into the organ, body cavity or lumen.

Today, most endoscopes are reused. This means that, after an endoscopy, the endoscope goes through a cleaning, disinfecting or sterilizing, and reprocessing procedure to be introduced back into the field for use in another endoscopy on another patient. In some cases, the endoscope is reused several times a day on several different patients.

While the cleaning, disinfecting and reprocessing procedure is a rigorous one, there is no guarantee that the endoscopes will be absolutely free and clear of any form of contamination. Modern day endoscopes have sophisticated and complex optical visualization components inside very small and flexible tubular bodies, features that enable these scopes to be as effective as they are in diagnosing or treating patients. However, the tradeoff for these amenities is that they are difficult to clean because of their small size, and numerous components. These scopes are introduced deep into areas of the body which expose the surfaces of these scopes to elements that could become trapped within the scope or adhere to the surface, such as body fluids, blood, and even tissue, increasing the risk of infection with each repeated use.

Endoscopes used certain parts of the body, such as forward viewing scopes use in the gastrointestinal tract have an added complexity in that they are in a bacteria rich environment. Typical gastroscopes and colonoscopes have a camera lens, light and working channels with distal openings exposed to the patient environment. These elements of the scope all create cleaning issues, including the risk that bacteria finds its way into the working channel and other hard to clean locations on the scope. This provides an opportunity for bacteria to colonize and become drug resistant, creating the risk of significant illness and even death for a patient. This infection risk is also present in the cable mechanisms that are used to articulate instruments passing through the working channel and in other aspects of current scope designs. Moreover, in addition to the health risks posed by bacterial contamination and patient-to-patient cross-contamination, the accumulation of fluid, debris, bacteria, particulates, and other unwanted matter in these hard-to-clean areas of the scope also impact performance, shortening the useful life of these reusable scopes.

Accordingly, it is desirable to provide devices which serve as convenient accessories for currently existing endoscopes to reduce the risk of contamination and infection, while also improving the performance of the endoscope. It is particularly desirable to provide an accessory for a forward-viewing scope that allows the user simultaneously to protect the working end from bacterial contamination and also enable instruments to exit out of the working end of the scope at different angles with ease.

SUMMARY

The present disclosure provides a coupler device for covering and sealing a portion of the working end of an end-viewing endoscope, such as a gastroscope, colonoscope or the like. The coupler device comprises a main body with a proximal end configured for attachment to a distal end portion of the end-viewing endoscope and a distal end portion that at least partially seals the distal end portion of the scope and allows for viewing of the surgical site. The coupler device protects the scope and its components, particularly the scope working channel and camera lens, to reduce the risk of debris, fluid and other matter ending up in the working channel, and other hard-to-clean areas potentially causing infection risk.

In certain embodiments, the endoscope comprises a light and a camera lens configured to provide a view in at least one direction substantially along the longitudinal axis of the scope (i.e., forward viewing). The main body of the coupler device preferably comprises a distal end portion having an open area substantially aligned with the light and camera lens of the scope to allow for viewing of the surgical site through the coupler device.

In one aspect of the invention, the coupler device includes an open area, cavity or channel that allows an instrument to pass through the coupler device from a working or biopsy channel of the endoscope to the surgical site. In other embodiments, the coupler device includes a flexible working channel extension that extends the working or biopsy channel of the scope and can be angularly adjustable.

The coupler device may be provided as a single-use disposable accessory to an endoscope that provides the user with the ability to advance an instrument through the coupler device to the surgical site, without exposing the distal end of the scope to bacteria, debris, fluid and particulate matter. In some embodiments, the device attaches to the end of the endoscope and covers the working or biopsy channel of the endoscope with a working channel extension in the coupler device, allowing an instrument to be passed down the working channel of the endoscope and into the working channel extension of the coupler device. The working channel extension can provide a seal against the scope working or biopsy channel, so instruments can be passed back and forth through the scope working channel and out the working channel extension of the coupler device without fluid and bacteria entering areas outside of the scope working channel. This seal is accomplished, in some embodiments, through an extension of the device working channel into the scope working channel, through a gasket on the end of the working channel extension, by way of a temporary glue, through pressure and the seal of the overall device against the distal end of the scope, through the selection of elastic and elastomeric materials, and other suitable and alternative means.

In certain embodiments, the instrument(s) passing through the endoscope and the coupler device may be articulated by a variety of suitable means, such as cables, elevators, piezo electric materials, micro motors, organic semiconductors, electrically activated polymers or other sources of energy or power, that are either disposed within the coupler device, on or within the endoscope, or external to both and suitably coupled to the instrument(s).

In other embodiments, the coupler device includes a flexible working channel extension that extends the working or biopsy channel of the scope and can be angularly adjustable. The flexible working channel extension may be adjustable by an elevator or cable passing through the endoscope. Alternatively, the coupler device may include its own actuator, such as an elevator, cable, or similar actuation means, for adjusting the working channel extension and thereby articulating instruments passing through the endoscope. The actuator may be powered by any suitable source of energy, such as a motor or the like. The source of energy may be coupled to the actuator either directly through the scope, or indirectly through magnetic, electric, or some other source of energy. The source of energy may be disposed within the coupler device, or it may be external to the coupler device (i.e., either disposed on the proximal end of the scope or external to the patient).

The working channel extension of the coupler device can be made of one or more materials with elastic properties. The materials can include biocompatible material(s) when the device is intended for medical applications, which may include, without limitation, elastic and elastomeric materials, as well as combinations of rigid and flexible materials, including silicone joined to polycarbonate and other materials joined to a biocompatible metal.

In some embodiments, the working channel extension of the coupler device may include an elastic biocompatible material that reduces the friction involving in passing devices through the working channel extension, which is joined to a biocompatible metal, such as a coil spring, hypotube, or braid, an additional elastic material that is joined to the biocompatible metal, to improve flexibility, reduce kinking and aid in sealing the working channel of the device against the endoscope's working channel.

In some embodiments, the device allows the user to articulate the working channel of the device in the direction preferred by the user of the endoscope, so that a wire, catheter or other instrument being advanced down the working channel of the endoscope can direct the wire or catheter or other instrument in a preferred direction different than the angle at which the instrument would exit the endoscope if the coupler device was not in place. This redirection of an instrument has the benefit of assisting with the navigation of the device, while not allowing fluid, debris, particulate matter, bacteria and other unwanted elements to enter hard to clean areas of the endoscope, especially at the distal end of the endoscope.

The benefits of the invention include allowing the physician to change the angle of exit, so that one or more devices can be turned to enter a particular body lumen, such as a biliary duct, pancreatic duct, or other hard to reach area in for example the colon or other areas of the GI tract, while sealing the distal end of the scope to prevent infection and the intrusion of debris and particulate matter into interior elements of the scope that are hard to reach to effectively clean and to provide a sterile coupler when a sterile accessory is beneficial, such as when tissue is penetrated creating a surgical site or when a bleed is present.

In some embodiments, the device may articulate instruments through the device through a cable in a sealed sheath that is attached to the flexible working channel extension in the coupler device, allowing the user to advance and retract the cable to move the working channel extension laterally relative to the longitudinal axis of the scope. Thus, the cable allows the user to change the angle of exit from the flexible working channel in order to direct an instrument to a desired direction.

In some embodiments, the device may have multiple cables so the angle of exit can be articulated in multiple directions, including in different quadrants, unlike with the current endoscope actuators, which can only deflect and therefore redirect an instrument in a single axis due to the limited travel of endoscope actuators, which can only be raised or lowered, but not moved from side to side or articulated into other quadrants. In some embodiments, the cable(s) may be attached directly to the working channel extension or to other devices that can be articulated and cause the working channel extension to change its angle of exit. In some embodiments, the articulation ability of the coupler device may be created with an actuator embedded in the coupler device, which is disposable and therefore thrown away after the procedure.

The articulation ability of the coupler device may also take place with elements that do not involve cables, including for example, piezo electric materials, micro motors, organic semiconductors, and electrically activated polymers. In some embodiments, the articulation ability of the coupler device may also take place with the transfer of force to the working channel extension through interlocking connectors that transfer force, wires that twist, slidable sheaths, and memory metals that change shape through the transfer of temperature. In some embodiments, the device includes a power connector or motors to deliver energy, including electromagnetic energy, to the device to cause a transfer in force to change the angle of exit from the coupler device as an instrument is passed through the device, or in advance of passing an instrument through the device. This transfer of force can include causing the device to rotate as it exits the working channel extension. The device may be navigated and articulated by the user directly, or as part of a robotic system in which the users input is translated through the system through various means, including cables, power connectors, motors, electromagnetic energy, slidable sheaths, haptics, computer-guided and directed input, and other means to direct and guide the device to its intended location, including to specific diagnosis and treatment objectives in a patient, or in non-medical applications, to a desired remote location.

In some embodiments, the device may be formed of an optically clear material that covers at least a portion of the end of the endoscope and seals the end of the endoscope, allowing visualization of the endoscope's camera without obscuring the view by the device. The optically clear material may also cover the endoscope's light guide to allow the light projected by the endoscope to illuminate the field of view of the endoscope. In some embodiments, the optically clear material may include navigation markers to orient the user when visualizing tissue, such as markers to identify the relative position of the scope as the user visualizes the tissue through the optically clear material.

In embodiments, the optically clear material may also include other markers to guide the user with confirmation of the accurate placement of the optically clear material over the endoscope's camera and, if applicable, over the endoscope's light guide.

In some embodiments, the device may be integrated into a scope and configured to be detachable and reusable for separate cleaning, including manual cleaning, in an autoclave, an ETO sterilizer, gamma sterilizer, and other sterilization methods.

The articulation aspect of the coupler device may include a locking feature or capability to affix the angle of exit in the working channel extension at a specific angle. In some embodiments, the specific angle of exit may be aimed at a specific point in the gastrointestinal tract, such as a location of interest within the colon, or the angle of exit may be affixed so that a wire or other instrument inside the working channel temporarily cannot be advanced, locking the instrument in position temporarily to aid in the exchange of instruments or to improve navigation of the instrument temporarily.

The device may include a disposable or reusable control mechanism that attaches to the endoscope to articulate the distal end of the coupler device to change the angle of exit from the working channel extension of the coupler device. In some embodiments, this control mechanism may also lock the angle of exit of the working channel extension or the working channel extension may be locked through elements in the endoscope itself, such as the elements that articulate the endoscope's elevator.

In some embodiments, the coupler device may cover the entire distal end of the endoscope, or may just cover hard to clean areas. In some embodiments, the coupler device may cover the distal end of the endoscope, or a portion thereof, or it may include a sheath attached to the coupler device which covers the entirety of the scope that is exposed to fluid, debris, particulate matter, bacteria and other unwanted elements.

In some embodiments, the device includes an anti-infective material. In another exemplary embodiment, the device includes an anti-infective coating. In still another embodiment, the device includes a coating that is hydrophobic. In yet another embodiment, the device is superhydrophobic. In even still another embodiment, the device is anti-infective and hydrophobic. Further yet in another embodiment, the device is anti-infective and superhydrophobic. In further still another exemplary embodiment, anti-inflammatory coatings are incorporated into the device.

The device may include a silver ion coating and a silver hydrogel applied, infused or made part of the device in the area that covers or goes around the scope elevators. The device may also include a valve or other element at the distal end of the catheter channel and may in embodiments have a valve in the working channel extension to prevent having fluid and debris traveling from the lumen back into the scope working channel. Alternatively, the device may include an electrical wire or other power transmission point to enable the creation of an electrical field across a silver ion coating to improve the activity of the silver ion coating or other coating to prevent infection.

In another aspect of the invention, a kit for use in an endoscopic procedure on a patient includes a device for use in an endoscopic procedure and a coupler device for covering and sealing a portion of the working end of an endoscope. The coupler device includes a flexible working channel extension that extends the working or biopsy channel of the scope. In certain embodiments, the kit further includes an endoscope, preferably a forward-viewing scope such a gastroscope, colonoscope or the like. The end-viewing scope includes a working channel, a light source and a camera.

In certain embodiments, the endoscope may further comprise an actuator for adjusting the angle of the working channel extension of the optical coupler. In one embodiment, the actuator comprises a cable extending through the shaft of the scope and configured for removable attachment to the working channel extension of the optical coupler.

In one embodiment, the kit further comprises a positioning system configured for facilitating the advancement of the endoscope through one or more internal body lumens, such as the small or large intestines. The positioning system preferably includes an over tube configured to slide over substantially the entire length of the endoscope and one or more inflatable balloon(s) configured for attachment to a portion of the outer surface of the endoscope or to the inner or outer surfaces of the over tube. The balloon(s) comprises an interior fluidly coupled to an internal lumen that extends through the over tube or the endoscope. The internal lumen is suitably coupled to a fluid delivery system external to the patient for inflation and deflation of balloon. Inflation of the balloon(s) facilitates advancement of the endoscope through the patient's intestines or other body lumens.

In another embodiment, the kit may include an inflatable balloon coupled to the endoscope and/or the coupler device. In certain embodiments, the inflatable balloon is removably coupled to the coupler device and includes a fluid delivery tube extending through, for example, the endoscope to allow for inflation or deflation of the balloon. The balloon can be used to facilitate advancement of the coupler device and the distal end portion of the endoscope through one or more internal body lumens, such as the pancreaticobiliary tract, the intestines, the patient's vasculature and the like.

In another embodiment, the kit further comprises a guidewire for use with the endoscope and the coupler device. The guidewire preferably comprises an elongate shaft sized for advancement through a working channel of the endoscope and the working channel extension or other articulating element of the coupler device. The guidewire comprises a distal tip sized to advance into a relatively narrow body lumen of the patient, such as pancreaticobiliary tract or other body lumen. The orientation of the guidewire may be adjusted by actuating the working channel extension of the coupler device or other articulating element in the coupler to change the angle that the guidewire exits the endoscope shaft.

In another embodiment, the kit comprises an access device configured for providing access to an interior of the patient's body through a natural orifice, such as a bite block, port, trocar or other similar device for assisting with the entry of the scope into the natural orifice, or in the case of a percutaneous penetration in the patient, such as a cannula, trocar or similar port that provides access through the patient's skin into a body cavity or less invasive surgery through an incision. For example, the device may include a cannula for providing access to a patient's gallbladder, biliary system, pancreas and/or liver in, for example, an endoscopic retrograde cholangiopancreatography procedure (ERCP), wherein the access device provides access through one of the major or minor papillas. Alternatively, the access device may be configured to provide access to the patient's vasculature (i.e., blood vessel) or another body lumen in the patient, such as the intestines. In certain embodiments, the endoscopic device may be configured to create the penetration, incision or other port on or within the patient's body (e.g., a trocar, papillotome, sphincterotome or the like). In other embodiments, the endoscopic device may be configured to maintain patency of an already-created opening or port in the patient's body (e.g., cannula).

In other embodiments, the kit further comprises an endoscopic device configured for advancement through an opening in the patient. For purposes of this disclosure, opening means any access port provided through a patient's skin into a body cavity, internal lumen (i.e., blood vessel), etc. and may include passage through natural orifices (such as the mouth, sinus, ear, urethra, anus and vagina) and through incisions, and port-based openings in the patient's skin, cavity, skull, joint, or other medically indicated points of entry. The endoscopic device may be configured to pass through a working channel within the endoscope (i.e., through the same access port as the endoscope) and further through the working channel extension or other passageway of the coupler device. Alternatively, the endoscopic device may be configured to pass through an opening that is separate from the endoscope access point.

In another embodiment, the kit further comprises a tissue collection device, such as a retrieval device configured for retrieving tissue or other matter from a patient's body, such as a polypectomy snare, tissue or polyp collection basket, retrieval basket or balloon for collecting stones, or other type of tissue collection device. The tissue collection device may also comprise biopsy forceps, suture removal forceps, needles or cytology brushes, including ultrasound guided or guided versions of collection devices. The tissue collection device is preferably configured to advance through the working channel of the endoscope and the working channel extension or other passageway of the coupler device In another embodiment, the kit further comprises a dilatation device configured for dilating a body tissue or lumen, a partially obstructed vessel or the like. For example, the dilatation device may comprise a catheter, such as angiographic catheter, arterial catheter, Foley catheter, stent (metal, plastic or bioabsorbable), a balloon, or the like, comprising an elongate flexible shaft for advancing through the patient's vasculature or other body lumen, and an inflatable device, such as a balloon, coupled to the distal end of the shaft. The dilatation device is preferably configured to advance through the working channel of the endoscope and the working channel extension or other passageway of the coupler device.

In yet another embodiment, the kit comprises a disposable endoscope for viewing within the body, including, without limitation during any procedure using remote visualization, such as merely for example, ERCP, colonoscopy, bronchoscopy, arthroscopic, ENT, OB/GYN and/or a laparoscopic procedure. In one preferred embodiment, the disposable endoscope comprises a cholangioscope configured for viewing into a very narrow channel, such as the central bile duct. The disposable endoscope is configured for advancing through the working channel of the end viewing endoscope and the working channel extension of the coupler device. Alternatively, the coupler device of the present invention may be adapted for covering and sealing a portion of the working end of the cholangioscope.

In another embodiment, the kit further comprises an instrument having an elongate shaft with a distal end portion configured for advancement through an opening into the patient. The instrument may include an endoscopic mucosal resection instrument, needle injector, Foley catheter, bipolar or monopolar electrosurgical or ultrasonic devices, snares, endoscopic staplers and other clamping or sealing instruments, arterial lines, drainage catheters, peripherally inserted central catheters, and other devices that penetrate and/or navigate in the body. The instrument may be configured to advance through the working channel of the endoscope and the working channel extension or other passageway of the coupler device.

In certain embodiments, the kit further comprises an implantable device configured to reside or in-dwell within the patient's body for a temporary or permanent period of time. The implantable device may include, for example, electrical nerve stimulators, defibrillators, drug delivery ports, endotracheal tubes, stents, pacemakers, joint implants, internal fixation devices, spinal implants and the like. In one such embodiment, the implantable device comprises a tubular support device for maintaining patency of a body lumen. The tubular support device may be, for example, a stent or similar device placed temporarily inside a blood vessel, canal, or duct to aid healing or relieve an obstruction, such as a plastic stent, self-expanding metallic stent (e.g., including via temperature change in the patient's body), bioabsorbable stent, ultrasound-guided stent or the like. The tubular support device is preferably configured to advance through the working channel of the endoscope and the working channel extension or other passageway of the coupler device.

In another embodiment, the kit further comprises one or more disposable valve(s) configured for attachment to a lumen in the endoscope for opening and closing access to the lumen. For example, the disposable valves allow the operator to open and close biopsy, irrigation, suction and/or air insufflation tubes coupled to the endoscope.

In yet another embodiment, the kit further comprises a bite block for use with an endoscope. The bite block comprises a front flange to overlap a patient's mouth and an opening configured to be received between the patient's lower and upper jaw and sized to provide access to the patient's oral cavity for an endoscope or the like.

The bite block serves to protect the patient's mouth from the endoscope and the endoscope from the patient's mouth (i.e., biting down during the procedure).

In some embodiments, the kit may include a procedure preparation device, such as a table drape, throat analgesic or the like. In other embodiments, the kit may include materials used post-procedure, such as cleaning brushes, swabs, sponges, tubing for irrigating and/or flushing the endoscope after the procedure, other cleaning and sterilization materials or devices, such as enzymatic cleaners, disinfectants, sterilizers, test trips or other sensors for determining the effectiveness of the cleaning procedure, contamination bags, scope transportation housings and the like.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 5 is a cutaway side view of the coupler device and a forward viewing scope in a first position.

FIG. 6 is a cutaway side view of the coupler device and a forward viewing scope in a second position.

FIG. 7 is a cutaway side view of the coupler device and a forward viewing scope in a third position.

FIG. 8 is an enlarged side view of a flexible membrane of the coupler device according to the present disclosure.

FIG. 10 is another enlarged side view of the working channel extension of FIG. 9.

FIG. 15 is a partial cutaway view of a biliary guidewire for use with an endoscope and the optical coupler of the present disclosure.

FIG. 27 is a schematic view of a compression device for an endoscopic procedure.

DETAILED DESCRIPTION

Figure 1:
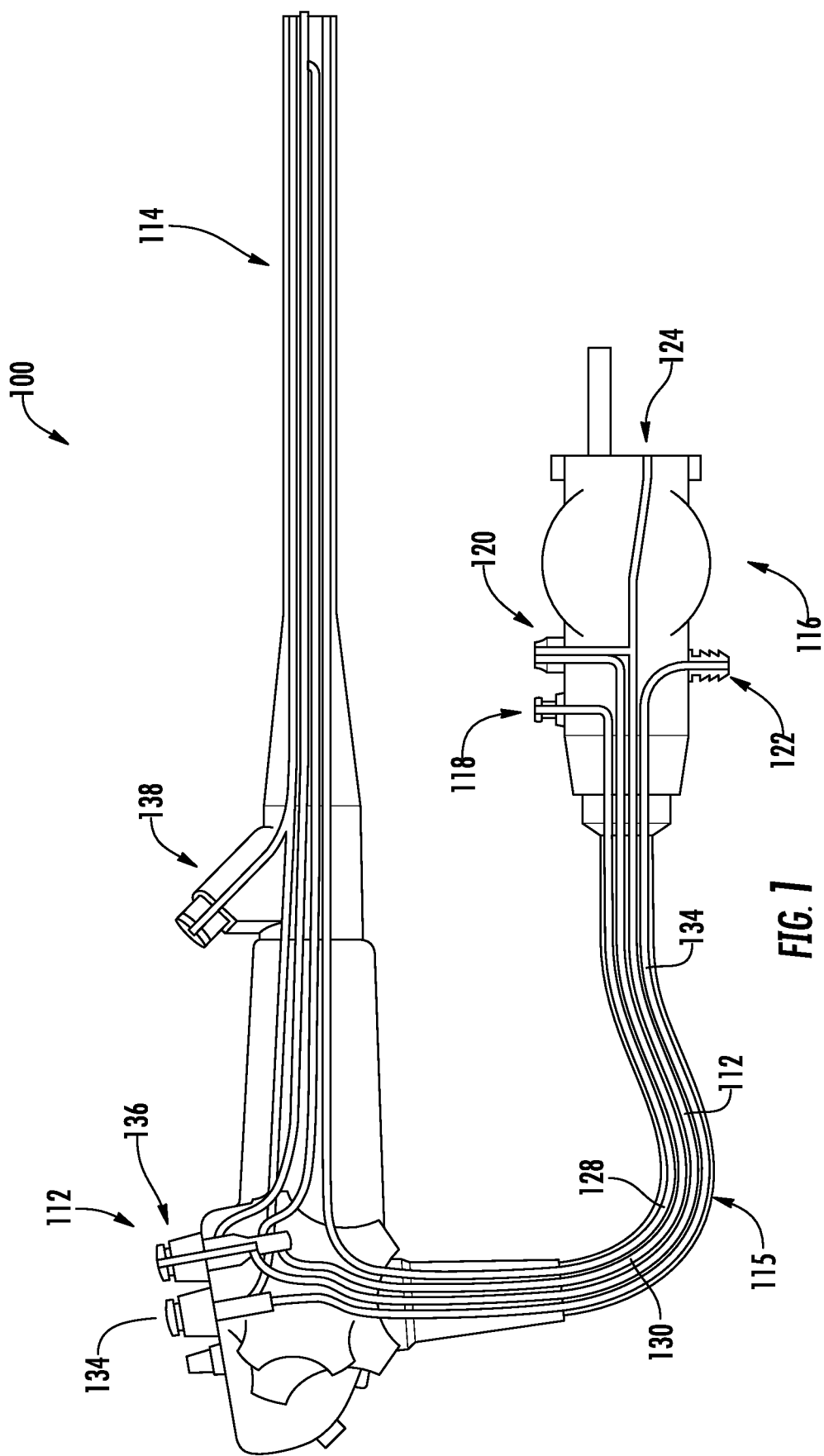
FIG. 1 is a partial cross-sectional view of the proximal portion of a representative endoscope according to the present disclosure.

This description and the accompanying drawings illustrate exemplary embodiments and should not be taken as limiting, with the claims defining the scope of the present disclosure, including equivalents. Various mechanical, compositional, structural, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described.

For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or illustrated components.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

While the following disclosure is primarily directed to a kit for use in an endoscopic procedure including a coupler device for an optical image endoscope, it should be understood that the features of the presently described kit may be readily adapted for use with a variety of resusable or disposable endoscopic scopes, instruments and devices.

The term "endoscope" in the present disclosure refers generally to any scope used on or in a medical application, which includes a body (human or otherwise) and includes, for example, a laparoscope, duodenoscope, endoscopic ultrasound scope, arthroscope, colonoscope, bronchoscopes, enteroscope, cystoscope, laparoscope, laryngoscope, sigmoidoscope, thoracoscope, cardioscope, and saphenous vein harvester with a scope, whether robotic or non-robotic.

When engaged in remote visualization inside the patient's body, a variety of scopes are used. The scope used depends on the degree to which the physician needs to navigate into the body, the type of surgical instruments used in the procedure and the level of invasiveness that is appropriate for the type of procedure. For example, visualization inside the gastrointestinal tract may involve the use of endoscopy in the form of flexible gastroscopes and colonoscopes and specialty duodenoscopes with lengths that can run many feet and diameters that can exceed 1 centimeter. These scopes can be turned and articulated or steered by the physician as the scope is navigated through the patient. Many of these scopes include one or more working channels for passing and supporting instruments, fluid channels and washing channels for irrigating the tissue and washing the scope, insufflation channels for insufflating to improve navigation and visualization and one or more light guides for illuminating the field of view of the scope.

Smaller and less flexible or rigid scopes, or scopes with a combination of flexibility and rigidity, are also used in medical applications. For example, a smaller, narrower and much shorter scope is used when inspecting a joint and performing arthroscopic surgery, such as surgery on the shoulder or knee. When a surgeon is repairing a meniscal tear in the knee using arthroscopic surgery, a shorter, more rigid scope is usually inserted through a small incision frequently on one side of the knee to visualize the injury, while instruments are passed through incisions on the opposite side of the knee. The instruments can irrigate the scope inside the knee to maintain visualization and to manipulate the tissue to complete the repair Other scopes may be used for diagnosis and treatment using less invasive endoscopic procedures, including, by way of example, but not limitation, the use of scopes to inspect and treat conditions in the lung (bronchoscopes), mouth (enteroscope), urethra (cystoscope), abdomen and peritoneal cavity (laparoscope), nose and sinus (laryngoscope), anus (sigmoidoscope), chest and thoracic cavity (thoracoscope), and the heart (cardioscope). In addition, robotic medical devices rely on scopes for remote visualization of the areas the robotic device is assessing and treating.

These and other scopes may be inserted through natural orifices (such as the mouth, sinus, ear, urethra, anus and vagina) and through incisions and port-based openings in the patient's skin, cavity, skull, joint, or other medically indicated points of entry. Examples of the diagnostic use of endoscopy with visualization using these medical scopes includes investigating the symptoms of disease, such as maladies of the digestive system (for example, nausea, vomiting, abdominal pain, gastrointestinal bleeding), or confirming a diagnosis, (for example by performing a biopsy, identifying bleeding, accessing inflammation, and identifying and confirming cancer) or surgical treatment of the disease (such as removal of a ruptured appendix or cautery of an endogastric bleed).

Referring now to FIG. 1, the kit of the present disclosure may include an optical viewing endoscope of the type described above. A representative endoscope 100 for use with the present disclosure includes a proximal handle 112 adapted for manipulation by the surgeon or clinician coupled to an elongate shaft 114 adapted for insertion through a natural orifice or an endoscopic or percutaneous penetration into a body cavity of a patient. Endoscope 100 further may include a fluid delivery system 116 coupled to handle 112 via a universal cord 115. Fluid delivery system 116 may include a number of different tubes coupled to internal lumens within shaft 114 for delivery of fluid(s), such as water and air, suction, and other features that may be desired by the clinician to displace fluid, blood, debris and particulate matter from the field of view. This provides a better view of the underlying tissue or matter for assessment and therapy. In the representative embodiment, fluid delivery system 116 includes a water-jet connector 118, water bottle connector 120, a suction connector 122 and an air pipe 124. Water-jet connector 118 is coupled to an internal water-jet lumen 126 that extends through handle 112 and elongate shaft 114 to the distal end of endoscope 100. Similarly, water jet connector 118, water bottle connector 120, suction connector 122 and air pipe 124 are each connected to internal lumens 128, 130, 132, 134 respectively, that pass through shaft 114 to the distal end of endoscope 100.

Endoscope 100 may further include a working channel (not shown) for passing instruments therethrough. The working channel permits passage of instruments down the shaft 114 of endoscope 100 for assessment and treatment of tissue and other matter. Such instruments may include cannula, catheters, stents and stent delivery systems, papillotomes, sphincterotomes, wires, other imaging devices including mini-scopes, baskets, snares and other devices for use with a scope in a lumen.

Proximal handle 112 may include a variety of controls for the surgeon or clinician to operate fluid delivery system 116. In the representative embodiment, handle 112 include a suction valve 135, and air/water valve 136 and a biopsy valve 138 for extracting tissue samples from the patient. Handle 112 may in some embodiments also include an eyepiece (not shown) coupled to an image capture device (not shown), such as a lens and light transmitting system. The term "image capture device" as used herein also need not refer to devices that only have lenses or other light directing structure. Instead, for example, the image capture device could be any device that can capture and relay an image, including (i) relay lenses between the objective lens at the distal end of the scope and an eyepiece, (ii) fiber optics, (iii) charge coupled devices (CCD), (iv) complementary metal oxide semiconductor (CMOS) sensors. An image capture device may also be merely a chip for sensing light and generating electrical signals for communication corresponding to the sensed light or other technology for transmitting an image. The image capture device may have a viewing end—where the light is captured. Generally, the image capture device can be any device that can view objects, capture images and/or capture video.

In some embodiments, endoscope 100 includes some form of positioning assembly (e.g., hand controls) attached to a proximal end of the shaft to allow the operator to steer the scope. In other embodiments, the scope is part of a robotic element that provides for steerability and positioning of the scope relative to the desired point to investigate and focus the scope.

Figure 2:
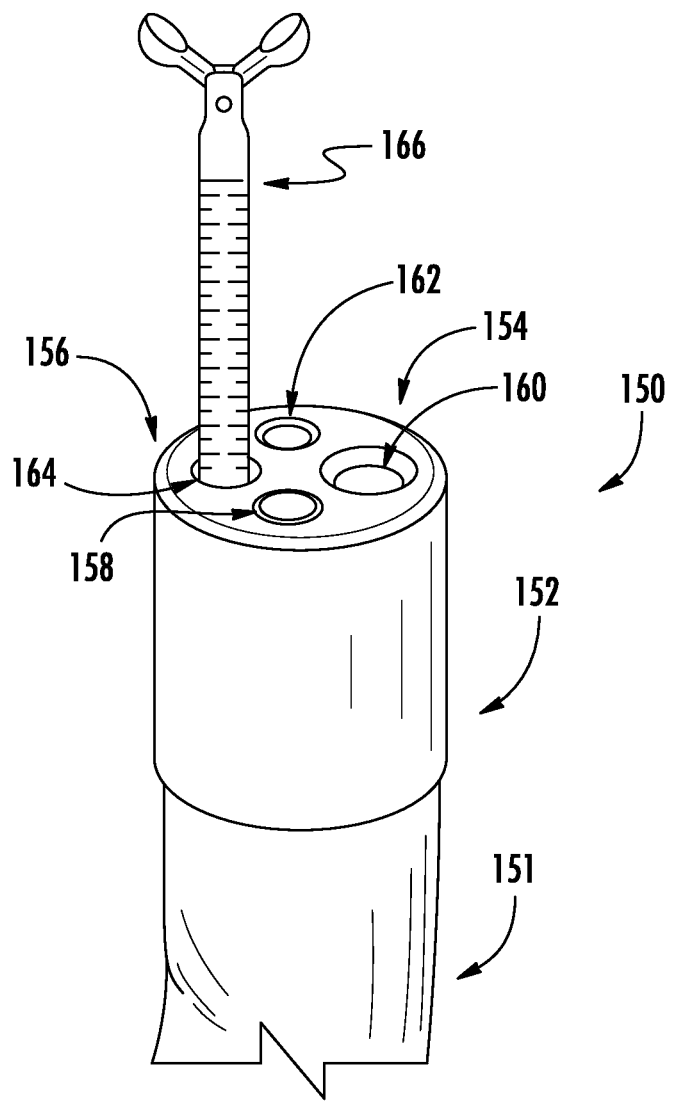
FIG. 2 is a side view of the distal end portion of an forward viewing endoscope according to the present disclosure.

Referring now to FIG. 2, a distal end portion of a forward or end-viewing endoscope 150 (e.g., a colonoscope) will now be described. As shown, scope 150 includes an elongate flexible shaft 151 with distal end portion 152 having a viewing region 154 and an instrument region 156, both of which face forward or towards the distal end of the longitudinal axis of shaft 151. Viewing region 154 includes a fluid port 158, a camera lens 160 and a light source 162 for providing a view of the surgical site in the patient. Instrument region 156 includes an opening 164 coupled to a working channel (not shown) within shaft 151 of scope 150. Opening 164 is configured to allow passage of instruments 166 from the working channel of scope 150 to the surgical site. Scope 150 also preferably includes an articulation mechanism for adjusting the angle that the instruments pass through opening 164. In the exemplary embodiment, the articulation mechanism comprises a cable (not shown) extending through shaft 151, although it will be recognized by those skilled in the art that the articulation mechanisms may include a variety of other components designed to articulate the instrument angle, such as an elevator or the like.

Figure 3A:
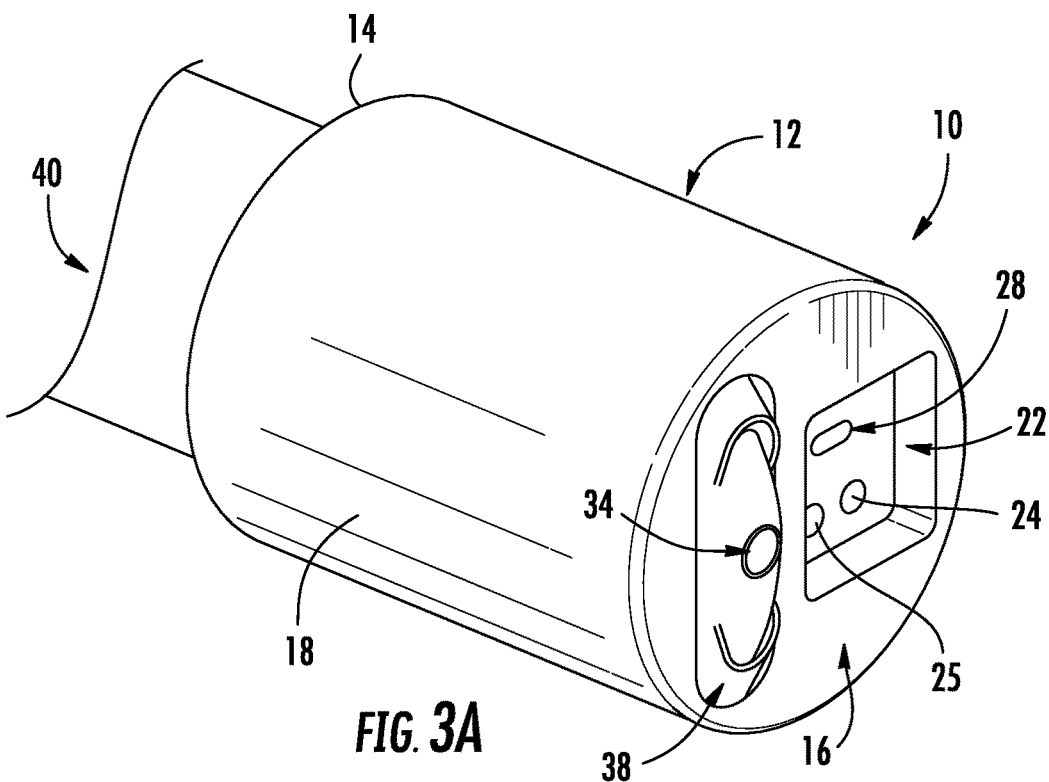
FIGS. 3A and 3B are isometric views of an exemplary embodiment of the coupler device of the present disclosure in use with a forward viewing scope.
Figure 3B:
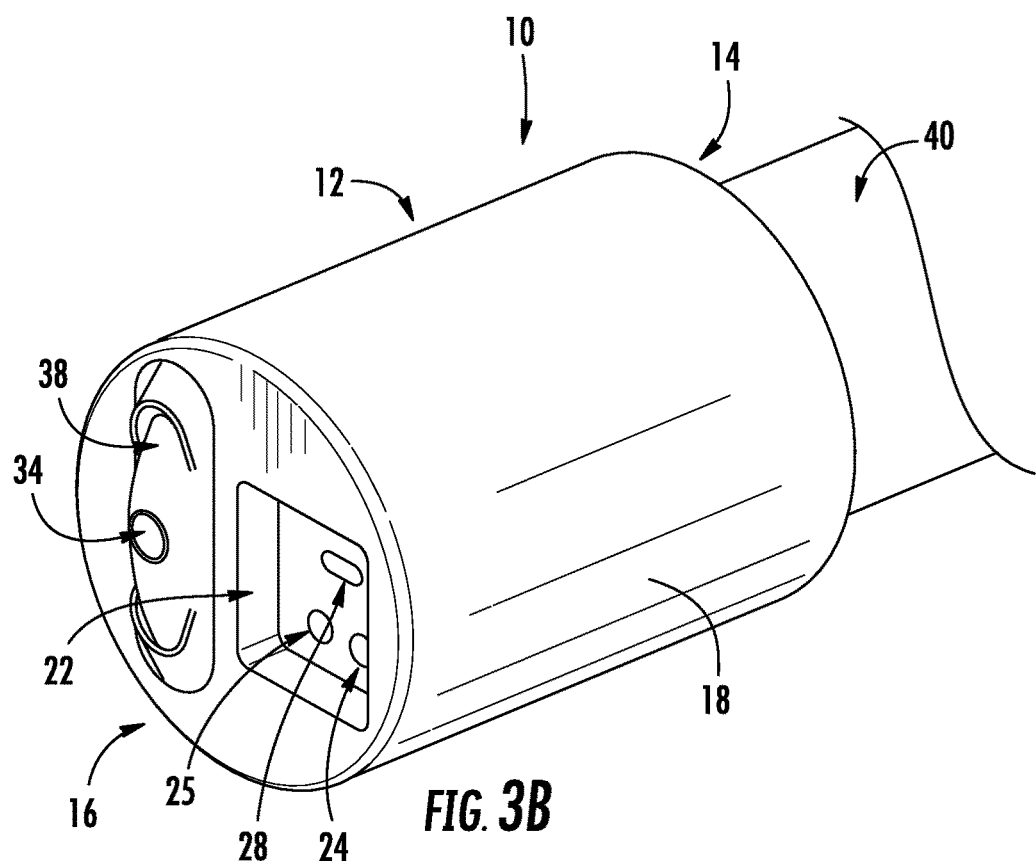

FIGS. 3A and 3B illustrate an exemplary embodiment of a coupler device 10 of the present disclosure. The coupler device 10 serves as an accessory component for currently existing endoscopes. The device seals and covers infection prone areas of the scope to prevent ingress of debris, fluid, or other unwanted matter that could lead to bacterial contamination and decreased performance of the scope. In addition, the coupler device 10 provides a flexible working channel for instruments to be inserted into the scope. The flexible working channel can be angularly adjustable with ease. As shown, in the preferred embodiments, the coupler device 10 may be used with an end viewing scope 40 or other end viewing scope instrument. It is understood, of course, that the coupler device 10 may be adapted for use with side-viewing scopes as well, such as a duodenoscope. In addition, the coupler device 10 of the present disclosure can be used with all types of scopes for different medical applications. The end viewing scope 40 shown here is merely for illustrative purposes.

As FIGS. 3A and 3B illustrate, the coupler device 10 may comprise a main body 12 with a proximal end 14 and a distal end 16 and an outer surface 18 surrounding main body 12. The proximal end 14 attaches onto a working end of an end viewing scope 40, extending the working end portion of the scope 40.

The distal end 16 may include a lens and light guide 24 and a scope washer opening 28, which is used to push fluid across the scope camera to wash debris off the camera and is also used to push air across the camera to dry the camera and insufflate the patient's gastrointestinal tract. Distal end 16 may further include an open area 22 substantially aligned with lens 25 and light guide 24 and scope washer opening 28 to facilitate forward or end viewing of the surgical site and to allow egress of fluid from scope washer opening 28 into the surgical site (and/or egress of air that may be passed over light guide 24 to dry the camera or that may be passed into the surgical site to insufflate a portion of the site).

Coupler device 10 further comprises a flexible working channel extension 34 having a proximal end 34a configured for attachment to a working channel of scope 40 and an open distal end 34b. Open distal end 34b of working channel extension 34 is surrounded by a flexible membrane 38. This flexible membrane 38 serves as a protective hood or covering for the working end of the coupler device 10, providing for flexible articulation while sealing out debris, fluid, bacteria or other unwanted matter.

Figure 4A:
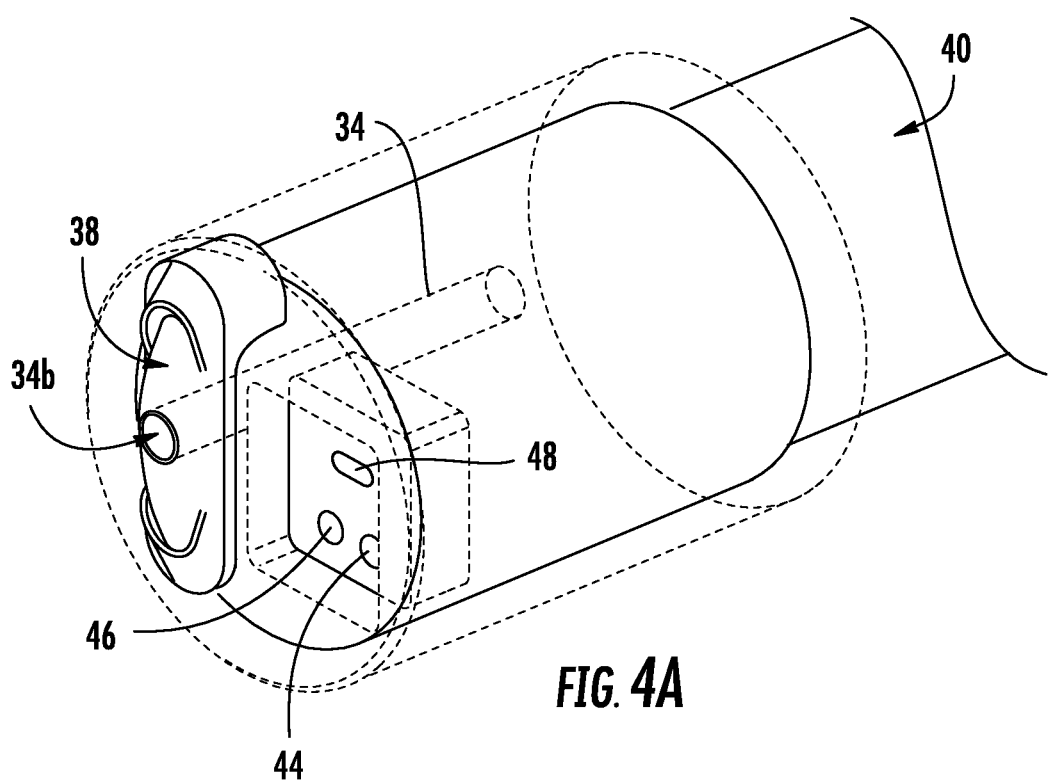
FIGS. 4A and 4B show partial cutaway views of the coupler device and a forward viewing scope of FIGS. 3A and 3B, respectively.
Figure 4B:
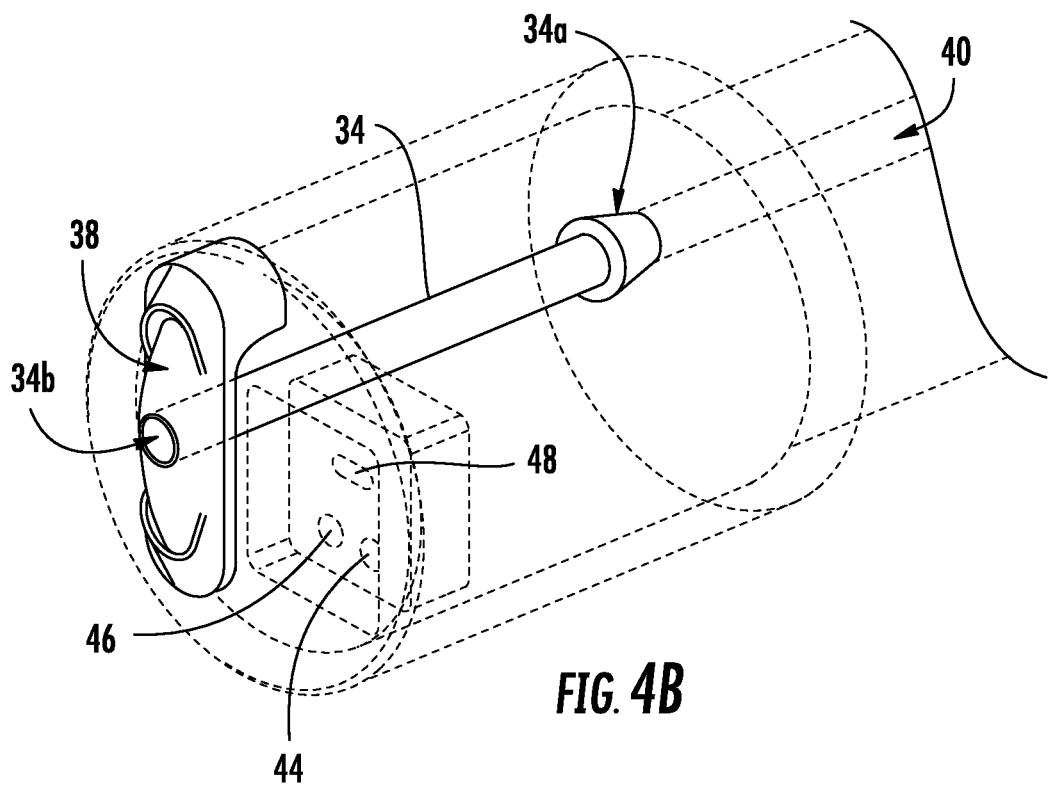

As shown in FIGS. 4A and 4B, the end viewing scope 40 may comprise a light guide 44, lens 46 and washer opening 48. The coupler device 10 cooperates with each of these components of the scope 40 to provide a fully functioning scope. The coupler device 10 does not interfere with the scope's ability to emit a clear image, but instead reduces the risk of contamination with each use. This benefit is achieved by providing a coupler device 10 which attaches to the working end components of the scope 40, and seals around the working end. The coupler device 10 provides an extension of the scope's working channel 42. The working channel extension 34 of the coupler device 10 in FIG. 3 is flexible and may contact the scope's working channel 42 by a sealed connection, as shown in FIG. 5, at the proximal end 34a of the working channel extension. The distal end 34b of the working channel extension 34 serves as an exit portal for instruments to pass through the scope 40 to reach different areas of the body.

Additionally, the coupler device 10 provides a further seal around the cable 54 of the scope. Because the coupler device 10 seals the elevator 54, risk of debris influx, fluids, bacteria and other matter build up behind the elevator and working channel is reduced significantly. This influx of debris, bacteria and other matter is believed to be the reason for drug resistant infections with current scopes today. While preventing influx, in embodiments the coupler device 10 advantageously maintains flexibility to move the working channel extension 34.

In certain embodiments, the coupler device 10 comprises a working channel (not shown) that is fixed and does not articulate. In these embodiments, coupler device preferably includes a seal around working channel of the scope. The working channel in the coupler device may be removably coupled to the scope's working channel, thereby providing an extension of the scope's working channel.

In use, the scope's working channel extension 34 permits passage of instruments down the scope working channel 42 and through and out the working channel extension 34 of the device 40 for assessment and treatment of tissue and other matter. Such instruments may include cannula, catheters, stents and stent delivery systems, papillotomes, wires, other imaging devices including mini-scopes, baskets, snares and other devices for use with a scope in a lumen. This working channel extension 34 is flexible enough that the cable 54 of the scope 40 can raise and lower the working channel extension 34 so that instruments can be advanced down and out of the working channel extension distal end (or exit portal) 34b of the scope 40 at various angles that are transverse to the longitudinal axis of scope 40.

Referring now to FIGS. 5-7, coupler device 10 comprises a disposable external sheath 60 that can receive an interior actuating cable 54 of the scope. This cable 54 can be attached to the flexible working channel extension 34 of the coupler device 10. As described below, actuation of the cable effects movement of the working channel extension 34. The external sheath 60 may be configured to attach directly to the scope 40, such as by winding around the outside of the scope or by a friction fit connection. In embodiments, multiple cables may be included in one or more sheaths to provide for articulation in other quadrants than the single axis articulation with elevators in current duodenoscopes.

As FIGS. 5 to 7 illustrate, in use when the cable 54 of the scope 40 is actuated, the flexible working channel extension 34 of the coupler device moves or adjusts to this actuation, either upwards or downwards such that the instruments exiting working channel extension 34 exit at an angle transverse to the longitudinal axis of scope 40. In FIG. 5, cable 54 is relaxed and allows working channel extension 34 to extend substantially parallel to the longitudinal axis of scope 40. In FIG. 6, the cable 54 has been withdrawn proximally such that the working channel extension 34 is raised and distal end 34b of working channel extension 34 is directed upwards. In this orientation, an instrument will exit working channel extension 34 in a direction slightly upward (relative to the drawing) from the longitudinal axis of scope 40. FIG. 7 illustrates cable 54 being advanced in the distal direction to translate working channel extension 34 downward (relative to the drawing) such that an instrument extends downward from distal end 34b.

Of course, it will be recognized that other configurations are possible. For example, the scope 40 may have two cables 54, with each cable located on either side of working channel extension 34. In this embodiment, proximal translation of the upper cable, for example, will cause working channel extension 34 to be oriented upwards or above the longitudinal axis of scope 40. Likewise, proximal translation of the lower cable will cause working channel extension 34 to be oriented downwards or below the longitudinal axis of scope 40. In other embodiments, the scope cables may be configured to pull working channel extension 34 laterally from side to side (relative to the drawing). In this manner, working channel extension 34 may be oriented at any angle 360 degrees around the longitudinal axis of scope 40. In some embodiments, the cable(s) may be attached directly to the working channel extension or to other devices that can be articulated and cause the working channel extension to change its angle of exit. In some embodiments, the articulation ability of the coupler device may be created with an actuator embedded in the coupler device, which is disposable and therefore thrown away after the procedure.

The articulation ability of the coupler device may also take place with elements that do not involve cables, including for example, piezo electric materials, micro motors, organic semiconductors, and electrically activated polymers. In some embodiments, the articulation ability of the coupler device may also take place with the transfer of force to the working channel extension through interlocking connectors that transfer force, wires that twist, slidable sheaths, and memory metals that change shape through the transfer of temperature. In some embodiments, the device includes a power connector or motors to deliver energy, including electromagnetic energy, to the device to cause a transfer in force to change the angle of exit from the coupler device as an instrument is passed through the device, or in advance of passing an instrument through the device. This transfer of force can include causing the device to rotate as it exits the working channel extension. The device may be navigated and articulated by the user directly, or as part of a robotic system in which the users input is translated through the system through various means, including cables, power connectors, motors, electromagnetic energy, slidable sheaths, haptics, computer-guided and directed input, and other means to direct and guide the device to its intended location, including to specific diagnosis and treatment objectives in a patient, or in non-medical applications, to a desired remote location.

As FIG. 8 shows, the ability of the distal end 34b of working channel extension 34 to shift along the distal end of the coupler device 10 is in part due to the fact that the distal end 34b is itself attached to a flexible membrane 38. This flexible membrane 38 comprises a plurality of loose folds or creases, allowing the excess material to stretch and bend as the elevator actuation forces the working channel extension to bend and shift in response. In addition, the flexible membrane 38 acts as a protective cover or hood for the working channel region of coupler device 10, preventing the ingress of fluids, debris, or other unwanted matter from getting inside the scope 140 and causing a bacterial contamination or the infusion of other unwanted fluid, debris or particulate matter.

It is contemplated that the coupler device 10 of the present disclosure may be configured for single, disposable use, or it may be configured for reuse. The coupler device 10 may be made of any biocompatible material, such as for example, silicone or another elastic or polymeric material. In addition, the material may be transparent. At least a portion of the coupler device 10 may be formed of a transparent material to provide a transparent covering of the scope camera and light source, thereby allowing unhindered performance of the scope 40.

In other embodiments, the coupler device 10 may also include a closable port (i.e., self-sealing) that allows for the injection of anti-adhesion, anti-bacterial, anti-inflammatory or other drug or infusible matter that prevents the adherence or colonization of bacteria on the scope. An applicator may be provided that is integrated into the coupler device 10 with a port for delivery of the infusible matter. Alternatively, the applicator may be separate from the coupler device 10 and applied to the distal end of the scope 40. The infusible matter may include forms of silver, including in a gel or other solution, platinum, copper, other anti-adhesion, anti-bacterial, anti-inflammatory or other drug or infusible matter that is compatible with the scope and coupler device materials and biocompatible for patient use.

In one exemplary embodiment, the device includes an anti-infective material. In another exemplary embodiment, the device includes an anti-infective coating. In still another embodiment, the device includes a coating that is hydrophobic. In yet another embodiment, the device is superhydrophobic. In even still another embodiment, the device is anti-infective and hydrophobic. Further yet in another embodiment, the device is anti-infective and superhydrophobic. In further still another exemplary embodiment, anti-inflammatory coatings are incorporated into the device. In other embodiments, the anti-inflammatory coatings may comprise a hydrophilic material.

In one exemplary embodiment, the device 10 may include a silver ion coating. In another embodiment, the device 10 may have a silver hydrogel applied, infused, or made part of the device 10 in the area that covers or goes around the scope elevators. In addition to silver having antimicrobial properties, silver can also conduct electricity. Thus, in still another embodiment, the device 10 may include an electrical wire or other power transmission point to enable the creation of an electric field across the silver ion coating to improve the ability of the silver ion coating to prevent infection. In some embodiments, the electrical wire or other power transmission point may also apply to other antimicrobial and conductive materials, including platinum and copper.

Figure 9:
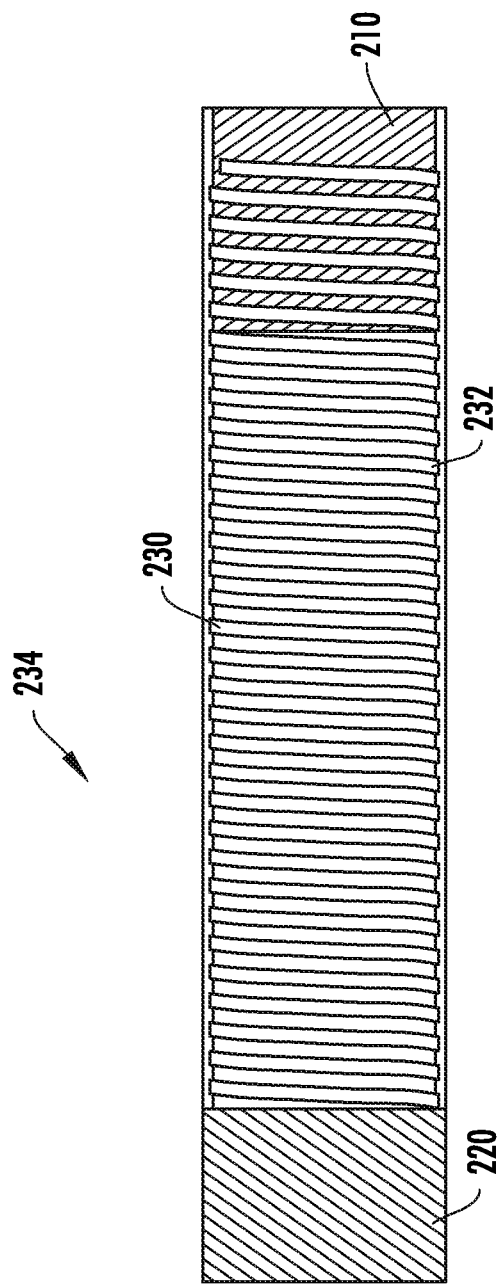
FIG. 9 is an enlarged side view of an exemplary embodiment of a working channel extension of the present disclosure.
Figures 11A, 11B:
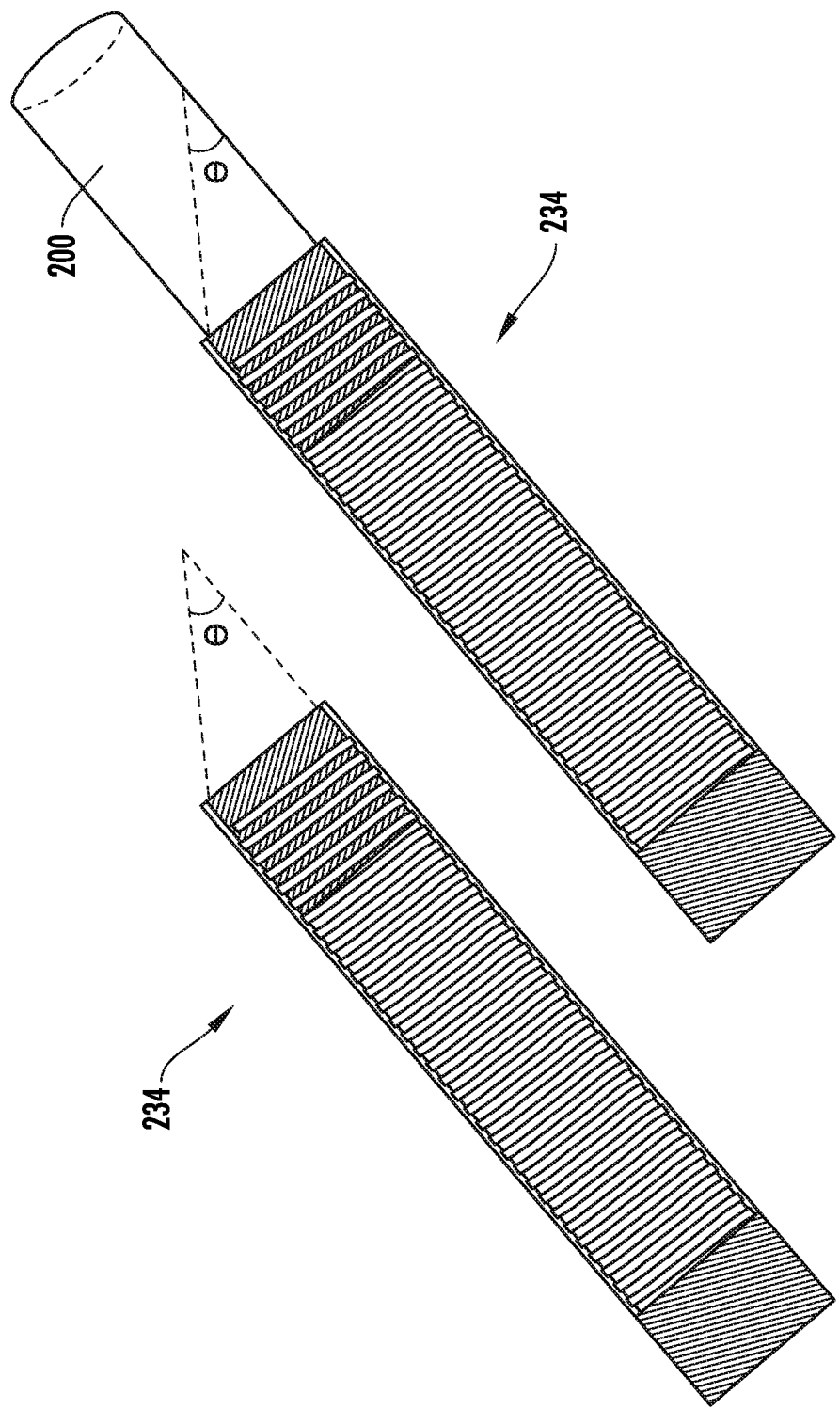
FIG. 11A is a perspective view of the working channel extension of FIG. 13.
FIG. 11B shows the working channel extension of FIG. 11A in use with an instrument.

FIGS. 8 and 9 show another embodiment of the working channel extension 234 of the present disclosure. As contemplated, the working channel extensions may comprise a combination of different materials. For example, as shown in FIG. 8, the working channel extension 234 may be formed of multiple elastic materials joined to a biocompatible metal. In some embodiments, one of the elastic materials may be PTFE and another elastic material may be a biocompatible elastic material that covers the biocompatible metal. In the example of FIG. 8, the working channel extension 234 may comprise an inner elastic material 210 and an outer elastic material. The outside of the working channel extension 234 may include a biocompatible metal 230, which may take the form of a coil, braid or winding 232. In one embodiment, the biocompatible metal may be encapsulated by one or more of the elastic materials.

In FIG. 9, the outer biocompatible elastic material 220 is formed to create a gasket 222 to seal the proximal end of the working channel extension against 234 the working channel of an endoscope, creating a seal to prevent the intrusion of unwanted bacteria, biomatter and other material into this sealed area.

In FIG. 10A, a working channel extension 234 is shown with an adjustable angle of exit θ for locking an instrument 200 in place. In this embodiment, when the angle of exit θ is adjusted, it creates compressive force in the working channel 234, locking an instrument 200 in place, as shown in FIG. 10B. This can be used to fixate an instrument while a wire is advanced through the instrument, or to fixate a wire, while a second instrument is exchanged over the wire.

Figure 12:
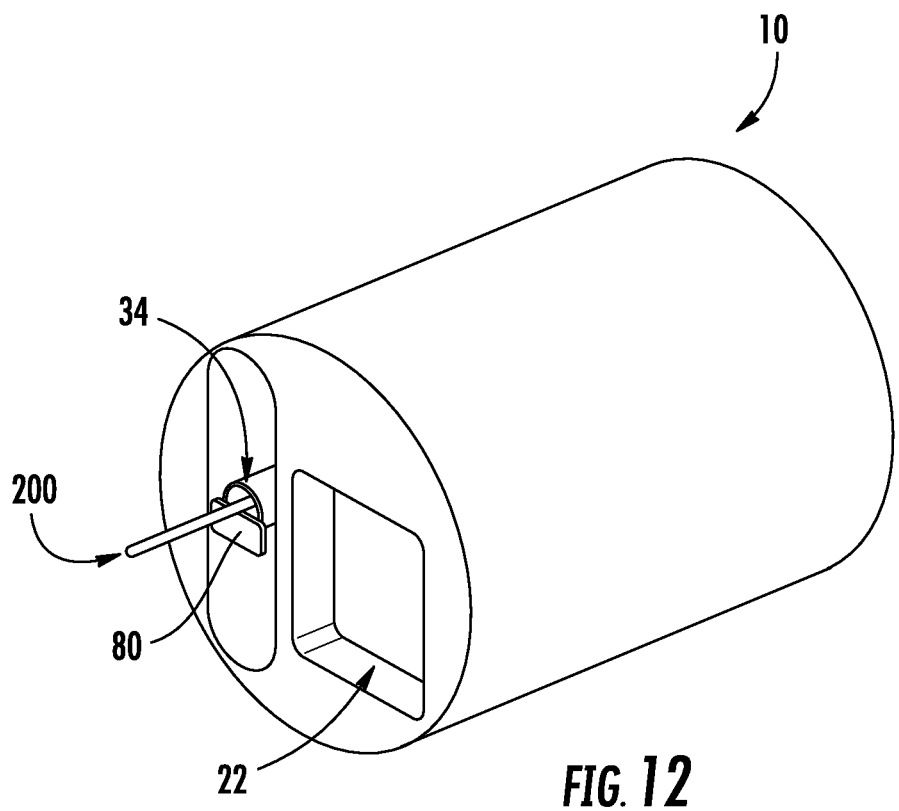
FIG. 12 is a perspective top-down view of the coupler device of FIG. 1 with a locking feature.

In FIG. 12, an alternative embodiment is shown for locking an instrument 200 in place. In this embodiment, the working channel extension 234 is raised to a point in which the instrument 200 in the working channel extension 234 is compressed against a lock 180 on the device 100, causing a change in the angle of exit of the working channel extension 234 and locking the instrument 200 in a fixated place in the working channel extension 234.

Figure 13:
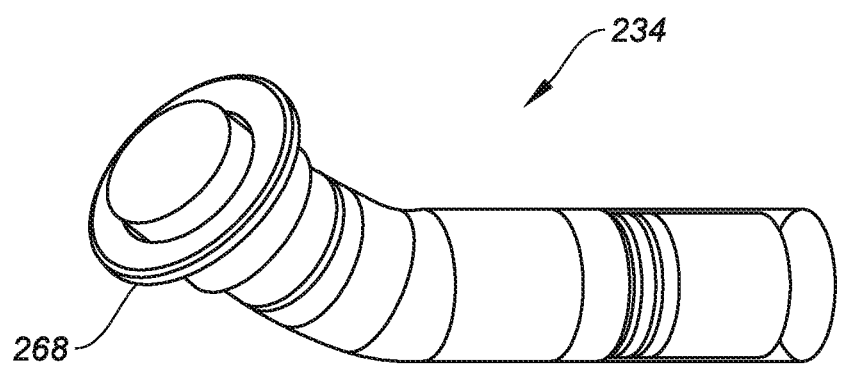
FIG. 13 is a perspective view of another exemplary embodiment of a working channel extension of the present disclosure.

In FIG. 13, an alternative embodiment of the working channel extension 234 is shown with a flange 268 for attaching the working channel extension to the membrane material 138 that is part of the device 10.

Figure 14:
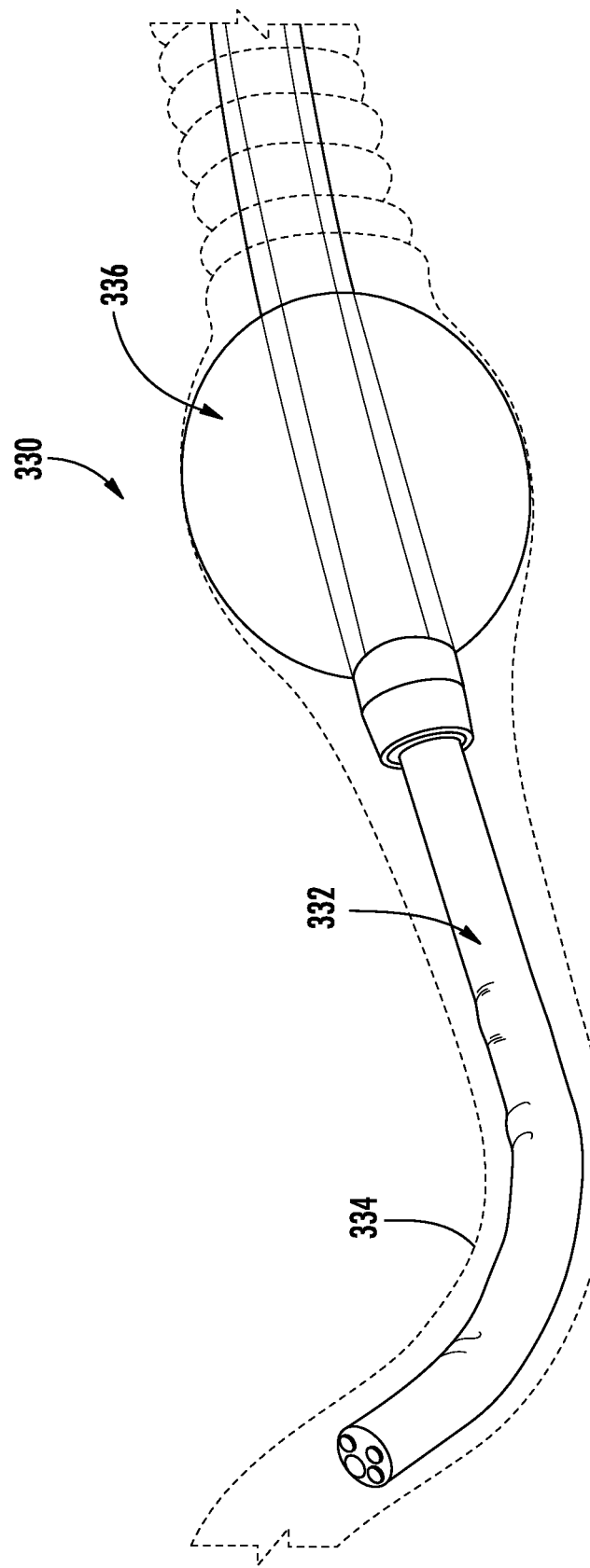
FIG. 14 is a perspective view of a positioning system for use with an endoscope and an optical coupler in a kit according to the present disclosure.

FIG. 14 illustrates a positioning system 330 for use in a kit including coupler device 10 (not shown in FIG. 14) and an endoscope 332 according to the present disclosure. Although endoscope 332 is shown as an end viewing scope, it will be understood that positioning system 330 can be used with any known scope, including side viewing scopes similar to those discussed above. As shown, positioning system 330 includes an overtube 334 designed to slide over the entire length of endoscope 332 An inflatable balloon 336 is configured for attachment to a portion of the outer surface of endoscope 332 or to the inner or outer surfaces of overtube 334. Balloon 336 comprises an interior fluidly coupled to an internal lumen that extends through overtube 334 or endoscope 332. The internal lumen is suitably coupled to a fluid delivery system external to the patient for inflation and deflation of balloon 336.

In use, inflation of balloon 336 serves to anchor overtube 334 within the patient's intestine. While the over tube 334 is anchored, the endoscope 332 can be advanced further into the small intestine. By withdrawing the overtube 334, the small intestine can be shortened and straightened to facilitate the passage of the inner endoscope 332 through the patient's intestines. The balloon 336 may then be deflated so that over tube 334 can be inserted further into the intestines. In the preferred embodiment, endoscope 332 preferably includes the coupler device 10, as described above.

Alternatively, the positioning system may comprise an inflatable balloon (not shown) configured for removable attachment to the distal end portions of either the endoscope 332 or coupler device 10. In this embodiment, balloon 336 is fluidly coupled via an internal lumen within the endoscope and/or coupler device 10 to a suitable fluid delivery system for inflation and deflation of the balloon with fluid and/or air.

In another embodiment, the kit may include an inflatable balloon coupled to the endoscope and/or the coupler device. In certain embodiments, the inflatable balloon is removably coupled to the coupler device and includes a fluid delivery tube extending through, for example, the endoscope to allow for inflation or deflation of the balloon. The balloon can be used to facilitate advancement of the coupler device and the distal end portion of the endoscope through one or more internal body lumens, such as the pancreaticobiliary tract, the intestines, the patient's vasculature and the like.

FIG. 15 illustrates a kit including a biliary guidewire 340, an endoscope 342 and coupler device 10 according to the present disclosure. As shown, guidewire 340 comprises an elongate shaft 344 sized for advancement through a working channel (not shown) in endoscope 342. Guidewire 340 comprises a distal tip 344 sized to advance into, for example, the gastrointestinal tract and/or the pancreaticobiliary tract 346 of a patient. Guidewire 340 may also be used in combination with coupler device 10 by passing the guidewire 340 through the working channel extension 34 of coupler device 10. The orientation of guidewire 340 may be adjusted by adjusting an elevator or cable in scope 342, which moves working channel extension 34 of coupler device 10 in an axial direction relative to the endoscope shaft, as described above. Coupler device 10 protects the scope and its components, particularly the scope elevator 50, to reduce the risk of debris, fluid and other matter ending up in the elevator and behind the elevator and the working channel, potentially causing infection risk.

Figure 16C:
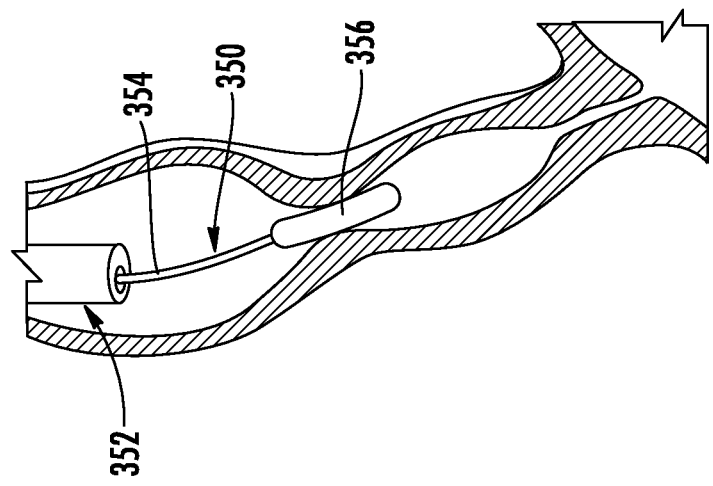
FIGS. 16A-16C illustrate a kit according to the present disclosure including, the optical coupler, an endoscope and a dilatation catheter.
Figure 16B:
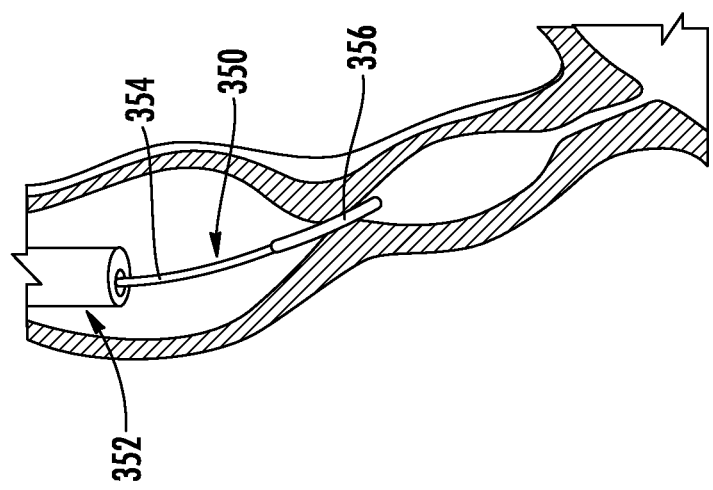
Figure 16A:
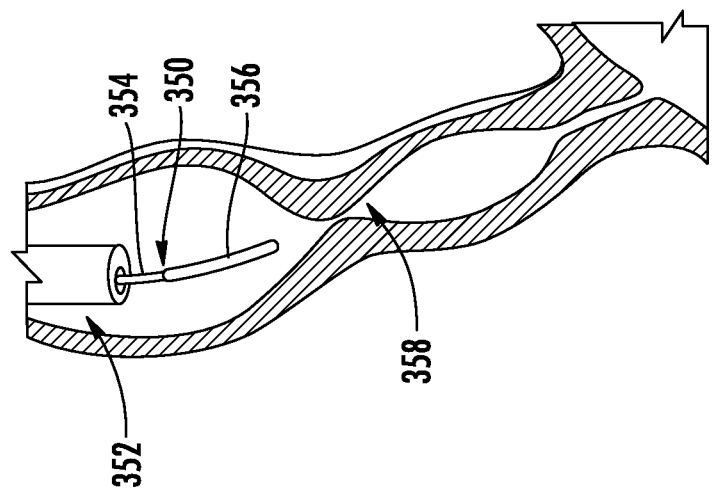

FIGS. 16A-16C illustrates a kit including a dilatation catheter 350, an endoscope 352 and the coupler device (not shown) according to the present disclosure. Although endoscope 352 is shown as an end viewing scope, it will be understood that dilatation catheter 350 can be used with any known scope, including side viewing scopes similar to those discussed above. As shown, catheter 350 includes an elongate flexible shaft 354 with an inflatable balloon 356 at its distal end. Balloon 356 is coupled to a fluid lumen (not shown) within shaft 354 that is suitably coupled to a fluid delivery system for delivering air or other fluid into balloon 356 to inflate the balloon. Catheter 350 may be used in combination with the scope and coupler device of the present disclosure to create or enlarge a passageway in the patient's body. For example, catheter 350 may be used with the scope and the coupler device for diagnosing and/or treating disorders in the liver, pancreas, gallbladder, spleen, duodenum, kidney or disorder in another lumen or organ or organ system.

FIGS. 16A-16C illustrate one example of dilatation catheter 350 used with an endoscope 352 and the coupler device (not shown in these figures) according to the present invention. As shown in FIG. 16A, catheter 350 is advanced through the working channel of endoscope 352 and through working channel extension 34 of coupler 10 until balloon 356 is distal of endoscope 352 and coupler device 10. Balloon 354 may then be advanced to a narrowed or stenosed region 358 of the body passage and inflated to enlarge the passageway (see FIGS. 16B and 16C). The entire procedure can be viewed by the camera and light in endoscope 352 through the open area in coupler device 10.

Figure 17:
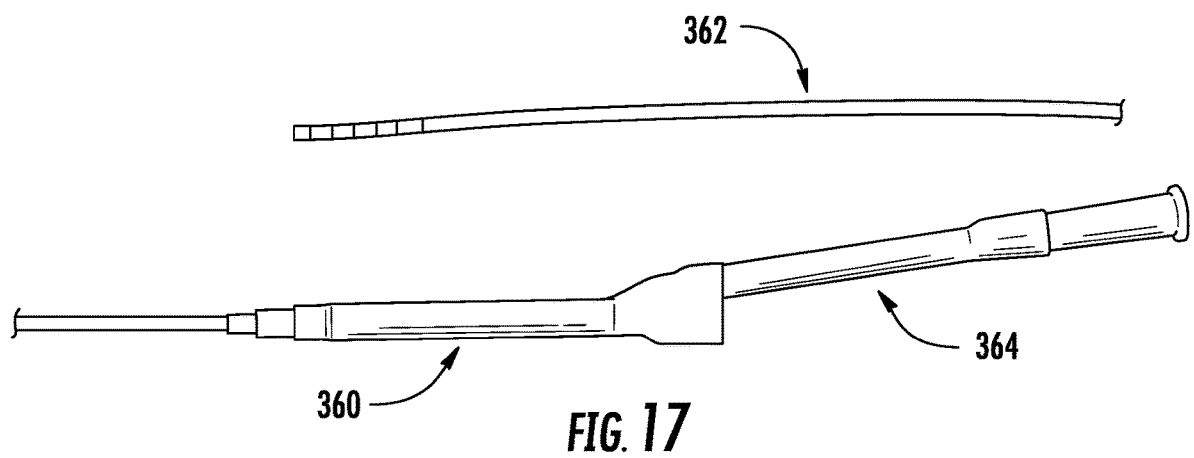
FIG. 17 is a perspective view of a cannula system for use in an ERCP procedure as part of a kit according to the present disclosure.

Referring now to FIG. 17, a cannula 360 for use in a kit according to the present invention is used in combination with coupler device 10 and the endoscopes of the present disclosure for gaining access to certain areas of the patient's lumen or specific assessment and/or surgical site, such as the patient's gallbladder, biliary system, pancreas and/or liver. In one embodiment, cannula 360 is configured for access through the major or minor papillas in, for example, an endoscopic retrograde cholangiopancreatography procedure (ERCP). Cannula 360 may be a single-lumen catheter for advancement of a guide wire 362, or it may have multiple lumens, for injection of contrast material or other fluids. Alternatively, cannula 360 may include a proximal adaptor 364, such as a Tuohy-Borst adaptor, that may function as a common port for both guidewire and contrast injection.

Figure 18:
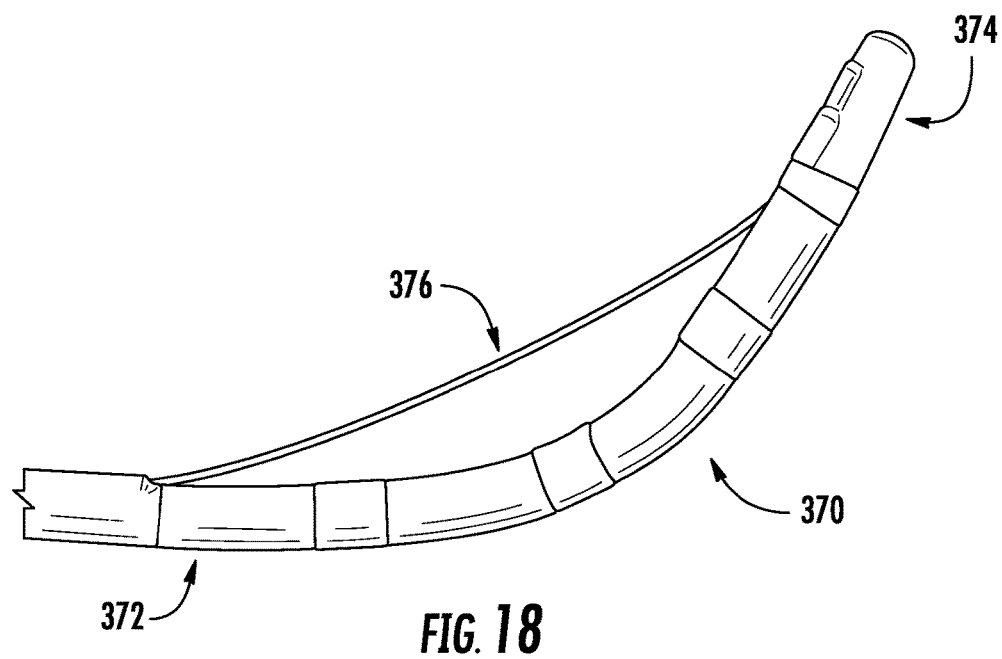
FIG. 18 is a perspective view of a sphincterotome for use in an endoscopic kit according to the present disclosure

FIG. 18 illustrates another endoscopic instrument 370 for use with the coupler device and endoscope of the present disclosure. As shown, instrument 370 includes an elongate flexible shaft 372 with a distal tip 374 and a cutting wire 376 extending to the region of distal tip 374. Cutting wire 376 has a proximal end coupled to a suitable electrosurgical power source for delivering electrosurgical energy to the surgical site. Instrument 370 may be configured as a sphincterotome, a papillotome or other suitable known electrosurgical catheter for use in endoscopic procedures. During a sphincterotomy, for example, activation of the power source causes electrical current to pass along an insulated portion of cutting wire 376 within the catheter to the exposed cutting wire 376. A retractable plunger on the control handle or other control mechanism (not shown) permits flexing of the catheter tip upward by pulling on cutting wire 376. This flexing assists with aligning the tip of the catheter with the proper orientation to the papilla and aligning the cutting wire 376 and maintaining contact of the wire with the papilla while the catheter is pulled back, incising the major or minor papilla.

In a preferred embodiment, instrument 370 is configured to passing through a working channel in an endoscope and through working channel extension 34 of coupler device 10. The angle of distal tip 374 can be adjusted, for example, with an elevator or cable in the endoscope which adjusts the working channel extension 34 within coupler device 10, as described above.

Figure 19:
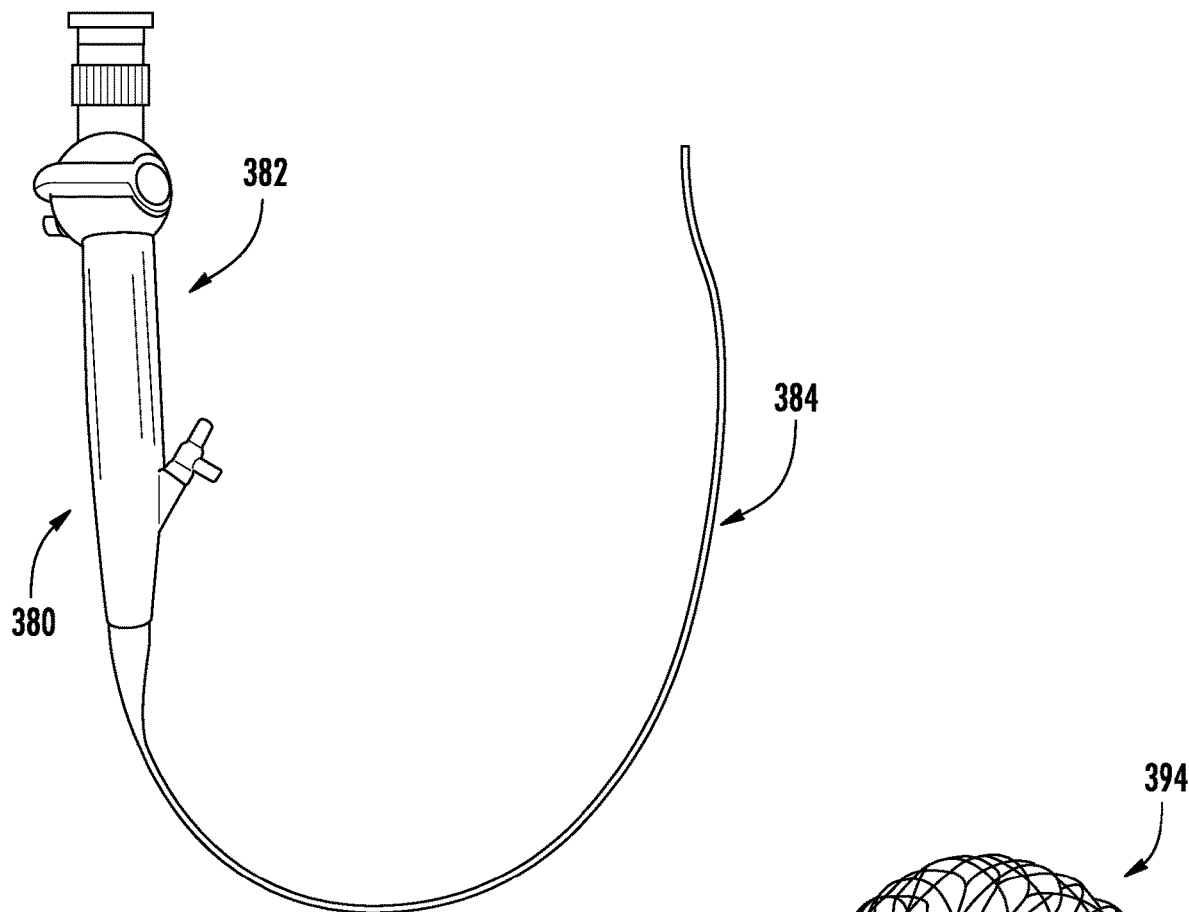
FIG. 19 is a perspective view of a cholangioscope for use in an endoscopic kit according to the present disclosure.

FIG. 19 illustrates another embodiment of an endoscope 380 for use in a kit according to the present disclosure. Coupler device 10 may be configured for use with endoscope 380 as discussed above. Alternatively, endoscope 380 may be used together with the coupler device 10 and endoscope 100 in an endoscopic procedure, such as procedure designed to diagnose or treat disorders of the bile duct, pancreas, liver duodenum or spleen. In this embodiment, endoscope 380 comprises a smaller disposable scope configured for advancement through the working channel of an end or side viewing scope such as the one described above in FIGS. 1 and 2. Disposable scope 380 is also configured for advancement through working channel extension 34 of coupler device 10 and can be articulated in any of the manners described above.

In an exemplary embodiment, endoscope 380 is a choledochoscope for use in examining and diagnosing the common bile duct of a patient. As shown, scope 380 includes a proximal handle 382 coupled to an elongate flexible shaft 384 sized for advancing into the common bile duct. Scope 380 further includes a thin fiberoptic cable for transmitting light to the surgical site, and a camera with a lens for viewing the site. In use, choledochoscope 380 may be used in combination with coupler device 10 to, for example, remove biliary tract stones from the common bile duct. For example, choledochoscope 380 may be passed directly into the bile duct such that a thorough exploration of the proximal and distal duct may be performed. Stones may be flushed out of the bile duct, removed directly with atraumatic graspers, forceps, or the like, or extracted using a snare, basket or other suitable device that is passed through choledochoscope 380 or an end viewing endoscope 100.

Figure 20:
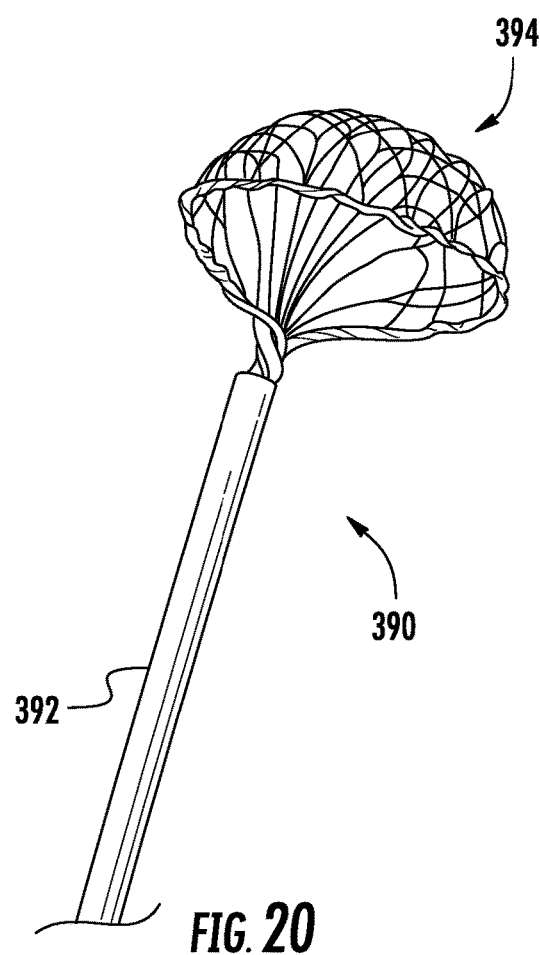
FIG. 20 is a perspective view of an extraction device for kidney stones for use in a kit according to the present disclosure.

FIG. 20 illustrates a stone entrapment and extraction device 390 for use with choledochoscope 380, coupler device 10 and/or endoscope 100. Extraction device 390 comprises an elongate shaft 392 and a capture basket 394 that may be advanced through the lumen of a suitable endoscope and through working channel extension 34 of coupler device 10. Once capture basket 394 has passed through the distal opening of working channel extension and delivered where clinically intended, it is expanded into the configuration shown in FIG. 26. Of course, device 390 may include components other than a basket for retrieving stones, such as a wire arrangement, a balloon or the like. Alternatively, any suitable grasping or biopsy forceps can be used with coupler device 10 and endoscope 100 to remove stones from the patient.

Figure 21C:
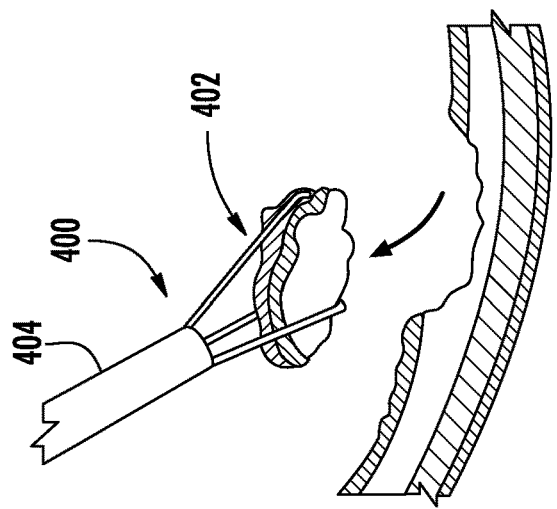
FIGS. 21A-21C are schematic view of instruments for use in a mucosal resection procedure according to the present disclosure.
Figure 21B:
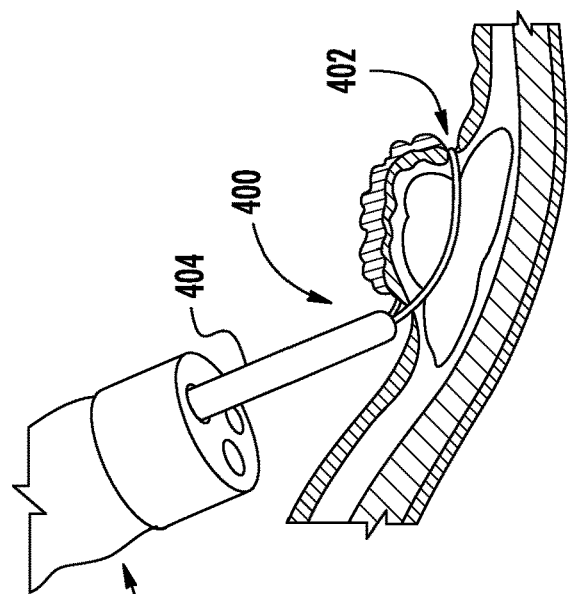
Figure 21A:
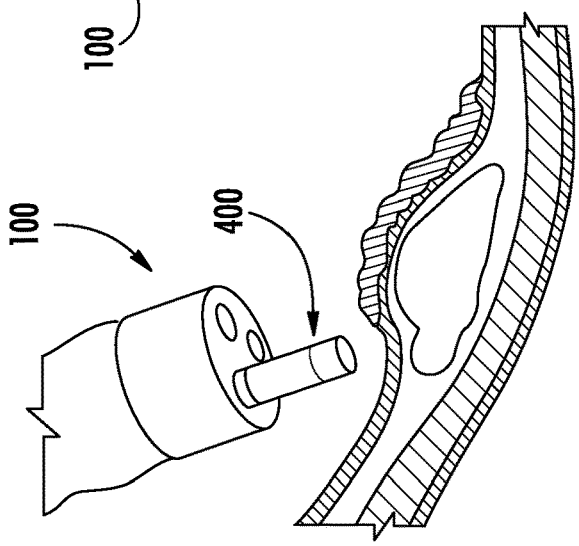

FIGS. 21A-21C illustrate a polyp or tissue removal device 400 for use with an endoscope 100 and the coupler device of the present invention. Note that although an end viewing scope is shown in the figures, tissue removal device 400 may be used with one of the side viewing scopes described above. Coupler device 10 (not shown in FIGS. 21A-21C) can be used to cover the tip of the endoscope such that tissue removal device 400 passes through working channel extension 34, as described above. Tissue removal device 400 can be, for example, a snare type device that includes a wire snare 402 at the distal end of an elongate shaft. The snare is configured for grasping and extracting tissue and/or polyps from the surgical site. Alternatively, tissue removal device 400 may comprise other suitable tissue removal components, such as baskets, balloons, forceps and the like.

Figure 22:
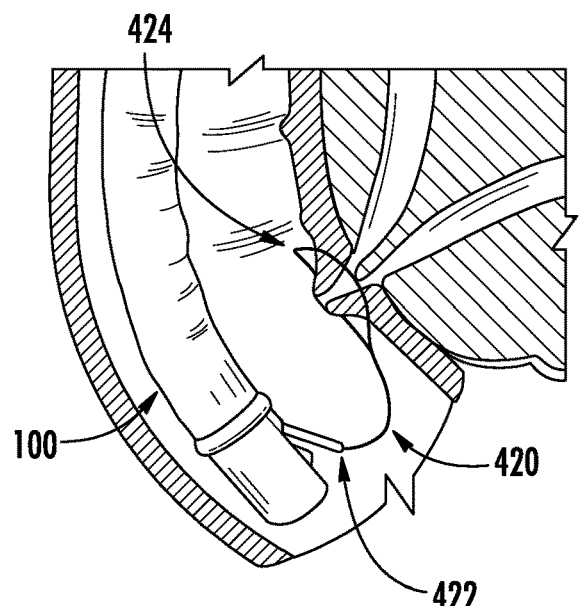
FIG. 22 is a schematic view of polypectomy snare instrument and an endoscope as part of a kit according to the present disclosure.

FIG. 22 illustrates a polypectomy snare 420 for use with endoscope 100 and the coupler device (not shown) of the present invention. As shown, a polypectomy snare 420 comprises an elongate shaft 422 designed to advance through the working channel of the endoscope and working channel extension 134 of coupler device. Snare 420 includes a wire loop 424 at its distal tip configured for passing over a polyp or other tissue matter. The wire loop 424 is coupled to an actuator at proximal end of the endoscope for actuating the loop and closing it onto the polp, resulting in cutting the polyp away from the patient's tissue. Wire loop 424 may be coupled to a power source external to the patient for passing electric current through loop to assist with the cutting procedure and to cauterize the tissue while removing the polyp.

Figure 23:
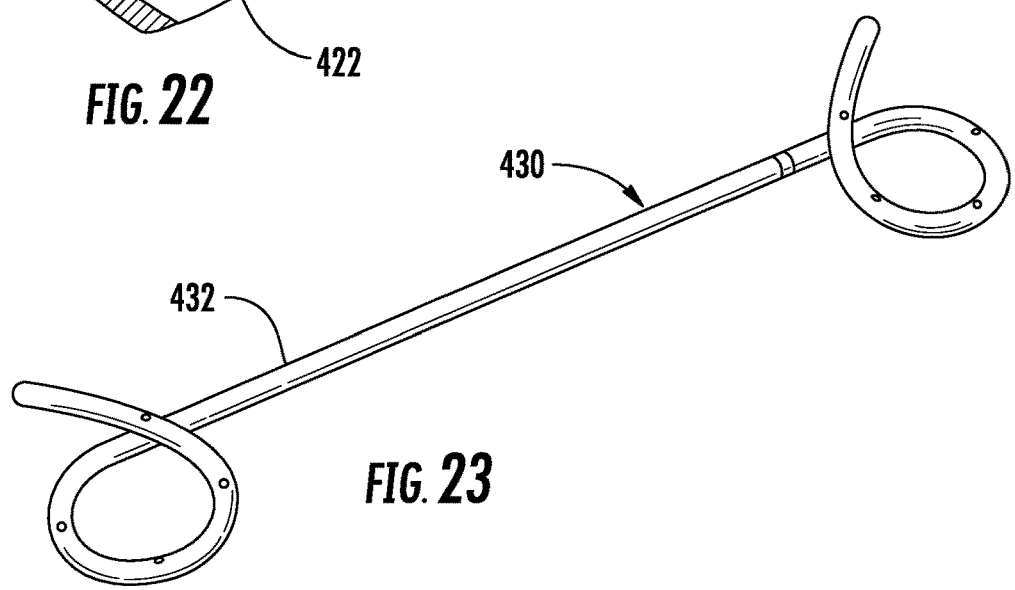
FIG. 23 is a perspective view of a biliary stent for use in with an endoscope and the optical coupler according to the present disclosure.

FIG. 23 illustrates a biliary stent 430 for use with an endoscope and the coupler device 10 in a kit according to the present invention. Stent 430 comprises a flexible metallic tube 432 configured to hold open a bile duct during or after an endoscopic procedure. Stent 430 may be placed within the bile duct and expanded therein to maintain patency of the bile duct such that fluids, such as bile (bilirubin) are able to flow into the duodenum to aid in digestion. Stent 430 is configured to advance through the working channel of the endoscope (typically with a guidewire) and through working channel extension 34 of coupler device 10. Once stent 430 has been passed through the distal open end of working channel extension 34, it can be put into position with bile duct and expanded so as to expand the bile duct channel. Stent 430 may be expanded through any suitable means knows in the art, such as body temperature (e.g., nitinol material) or actuating mechanisms. Stent 430 may comprise any suitable material, such as plastic, temperature-based self-expanding materials (e.g. nitinol), bioabsorbable materials or the like.

Figure 24:
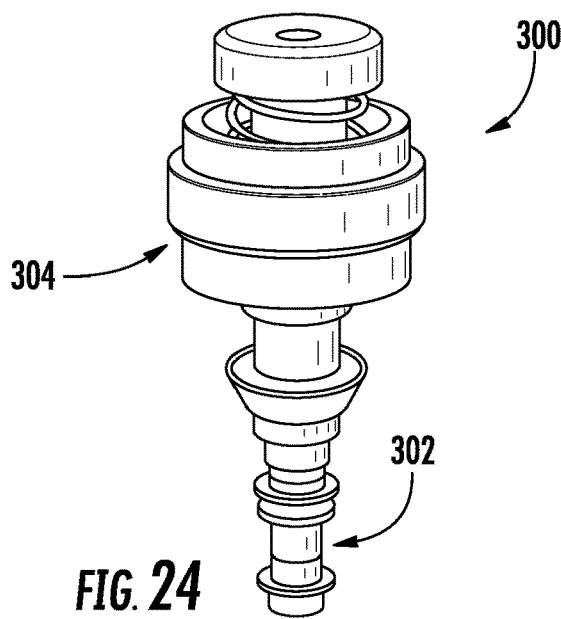
FIG. 24 is a perspective view of a disposable valve for use with an endoscope and coupler device according to the present disclosure.

FIG. 24 illustrates a disposable valve 300 for use in a kit including the endoscope 100 and coupler device 10 of the present disclosure. Disposable valve 300 is configured for attachment to a valve in endoscope 100 for opening and closing access to an internal lumen within the endoscope. As shown, disposable valve 300 comprises a stem 302 for sealing a lumen in an endoscope valve, maintain a suction force and preventing fluid from passing through the lumen, and an adjustable valve 304 for opening the lumen such that fluids may pass therethrough. Valve 300 may be configured for opening and closing biopsy, irrigation, suction and/or air insufflation valves coupled to the endoscope. Valve 300 is disposable and intended for single-use on one surgical procedure or patient.

Figure 25:
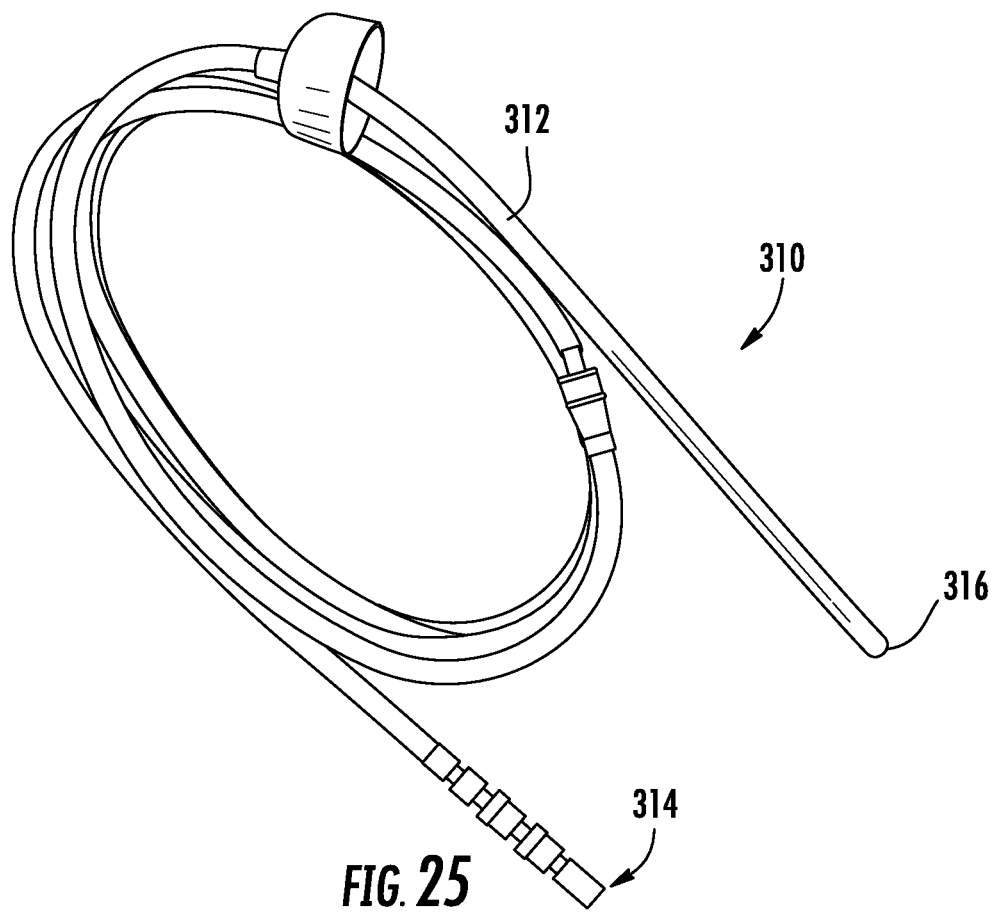
FIG. 25 is a perspective view of disposable tubing for use with an endoscope and the coupler device of the present disclosure.

FIG. 25 illustrates disposable tubing 310 for use in a kit including the coupler device 10 and an endoscope according to the present disclosure. As shown, tubing 310 comprises an elongate flexible tube 312 with an internal lumen for passing fluid therethrough, and a distal fitting 314 configured for attachment to an endoscope valve or a disposable valve, such as the one described above in reference to FIG. 20. Tubing 310 further comprising a proximal end 316 for attachment to a suitable fluid delivery system, such as a sterile water bottle, irrigation pump, suction device, air or CO2 pump or the like. Tubing 310 is designed as a single-use disposable device and may include multiple tubes.

Figure 26:
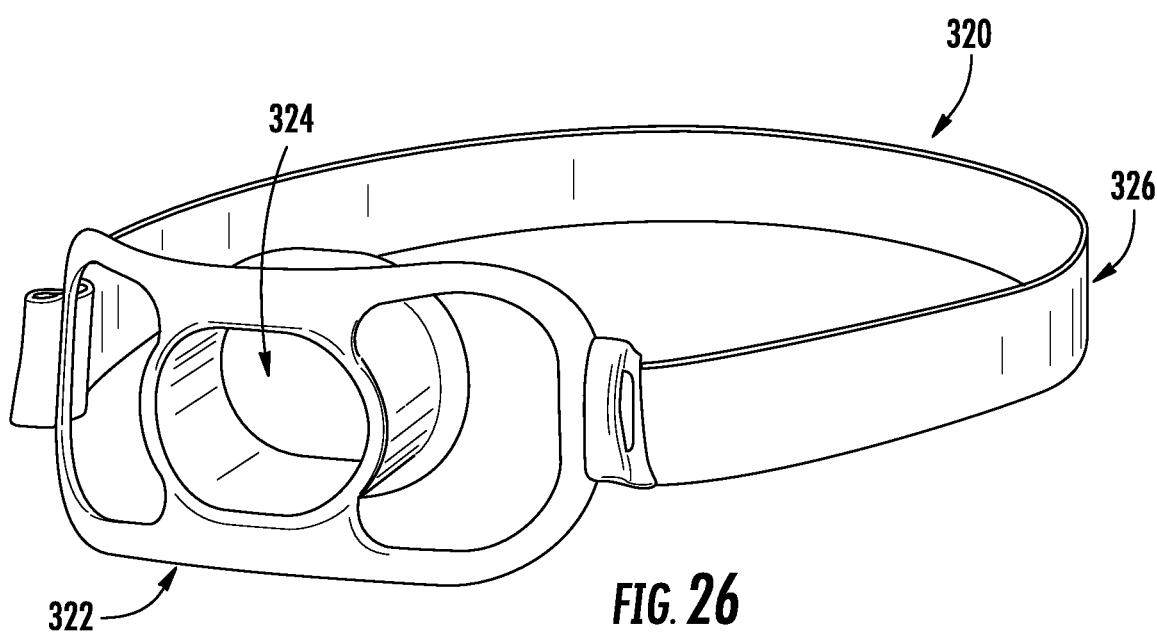
FIG. 26 is a perspective view of a bite block for use with an endoscope and the optical coupler of the present disclosure.

FIG. 26 illustrates a bite block 320 for use in a kit including coupler device 10 and an endoscope according to the present disclosure. As shown, bite block 320 includes a front flange 322 to overlap a patient's mouth and an opening 324 configured to be received between the patient's lower and upper jaw and sized to provide access to the patient's oral cavity for an endoscope or the like. Bite block 320 may further include a strap 326 or other suitable device for wrapping around the patient's head to secure front flange 322 in place. Bite block 320 serves to protect the patient's mouth from the endoscope and the endoscope from the patient's mouth (i.e., biting down during the procedure).

FIG. 27 illustrates an external anatomic support band 440 for use with the endoscope 100 and coupler device 10 in a kit according to the present invention. Support band 440 is an abdominal compression device configured for wear by patients undergoing endoscopic procedures, such as colonoscopy. In the exemplary embodiment, support band 440 is configured to provide sustained, adjustable pressure to splint the patient's sigmoid and transverse colon 442, which allows for faster and easier endoscope advancement. During colonoscopy, looping is a frequent challenge. It occurs as the endoscope is advanced forward, which causes stretching and distension of the colon in response to the physician's efforts to advance the scope forward through the colon.

In other embodiments, the kit may include other devices for use with the endoscope and coupler device of the present disclosure, such as cytology brushes, biopsy forceps or needles, needle injectors, or the like. A needle biopsy is a procedure to obtain a sample of cells from your body for laboratory testing. Common needle biopsy procedures include fine-needle aspiration and core needle biopsy. In certain embodiments, an ultrasound-guided biopsy device 410 can be used with the endoscope(s) and coupler device 100 of the present disclosure In certain embodiments, the kit includes an ultrasound, x-ray or other lithotripter device configured for transmitting sounds waves (e.g., shock waves) through a patient's outer skin surface to a target site within the body. For example, the lithotripter may focus shock waves onto stones to break up the stones into smaller fragments that can be retrieved by one of the devices or methods discussed above, or naturally passed out of the body through urine. The lithotripter may be used in conjunction with the endoscope and optical coupler of the present disclosure for treating stones and/or or disorders of the GI tract.

The kit of the present disclosure may also include a variety of devices used to prepare for an endoscopic procedure with the endoscope and coupler device of the present disclosure, such as table drapes, throat analgesics, tissue/polyp collection baskets and the like.

The kit of the present disclosure may also include a variety of other devices used after an endoscopic procedures, such as cleaning brushes, swabs and/or sponges, disposable tubing for irrigating and flushing an endoscope, enzymatic cleaners, disinfectants, and other devices and agents for sterilizing and/or disinfecting medical devices, test strips or other sensors for determining the effectiveness of such cleaning devices (i.e., detecting the presence of proteins, biomatter, bacteria, fungi, viruses or other pathogens), scope housings for transporting scopes to and from, for example a reprocessing location, contamination bags and the like.

Suitable sensors for use with the present invention may include PCT and microarray based sensors, optical sensors (e.g., bioluminescence and fluorescence), piezoelectric, potentiometric, amperometric, conductometric, nanosensors or the like. The kit further include an indicator, such as a display, coupled to the sensor(s) and configured to indicator the presence of pathogens, liquids or other particulars detected by the sensor. The indicator may be any suitable chemical indicator validated for sterilization procedures that undergoes a physical or chemical change visible to the human eye after exposure to certain parameters. The indicator and sensor may be part of the same device, or separate from each other.

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A coupler device configured for use with a forward viewing endoscope having a working channel with a distal end, a light and a camera lens, comprising:
    a main body comprising a distal end and a proximal end configured for removable attachment to a distal end portion of the endoscope by a sealed connection;
    a flexible working channel extension within the main body, the working channel extension having an open distal end and a proximal end that is configured for attachment to the distal end of the working channel of the endoscope;
    a sheath extending through the main body of the coupler device, wherein the sheath is coupled to the flexible working channel extension and configured to receive a cable therethrough for moving the working channel extension from a first position, wherein the proximal end of the working channel extension extends from the distal end of the working channel of the endoscope substantially parallel to a longitudinal axis of the endoscope, to a second position, wherein the proximal end of the working channel extension extends from the distal end of the working channel of the endoscope at an angle to the longitudinal axis of the endoscope; and
    wherein the coupler device is configured to allow a view of tissue located distal to a distal end of the endoscope.

2. The coupler device of claim 1, further comprising a mechanism for articulating an instrument passing through the endoscope.

3. The coupler device of claim 1, wherein the working channel extension is capable of angular adjustment.

4. The coupler device of claim 3, wherein the working channel extension is configured for angular adjustment by actuation of the endoscope.

5. The coupler device of claim 3, wherein the coupler device further comprises an actuator for articulating the working channel extension.

6. The coupler device of claim 1, wherein the coupler device is configured for use coupling to the endoscope such that the light and the camera lens of the endoscope provide a view through the coupler device in at least one direction substantially parallel to the longitudinal axis of the endoscope.

7. The coupler device of claim 3, wherein the main body of the coupler device comprises a distal end portion having an open area and the coupler device is configured to couple to the endoscope such that the open area is substantially aligned with a-view provided by the light and the camera lens of the endoscope.

8. The coupler device of claim 2, wherein the working channel extension extends substantially parallel with the longitudinal axis of the endoscope when the coupler device is attached to the distal end portion of the endoscope, the working channel extension being configured for lateral angular adjustment to one or more orientations transverse to the longitudinal axis of the endoscope.

9. The device of claim 2, wherein the coupler device is configured to removably attach to the endoscope and the endoscope includes a mechanism for angular adjustment of the working channel extension.

10. The device of claim 1, wherein the coupler device comprises an elastic or elastomeric material.

11. A kit for use in an endoscopic procedure, the kit comprising:
   a forward viewing endoscope having a distal end, a working channel with a distal end, a light and a camera lens, wherein the endoscope provides a view of tissue distal to the distal end of the endoscope; and
   a coupler device comprising:
      a main body comprising a distal end and a proximal end configured for removable attachment to a distal end portion of the endoscope by a sealed connection;
      a flexible working channel extension within the main body, the working channel extension having an open distal end and a proximal end that is configured for attachment to the distal end of the working channel of the endoscope;
      a sheath extending through the main body of the coupler device, wherein the sheath is coupled to the flexible working channel extension and configured to receive a cable therethrough for moving the working channel extension from a first position, wherein the proximal end of the working channel extension extends from the distal end of the working channel of the endoscope substantially parallel to a longitudinal axis of the endoscope, to a second position, wherein the proximal end of the working channel extension extends from the a distal end of the working channel of the endoscope at an angle to the longitudinal axis of the endoscope; and
   wherein the coupler device is configured to allow said view of tissue distal to the distal end of the endoscope by the endoscope.

12. The kit of claim 11, further comprising a mechanism for articulating an instrument passing through the working channel of the endoscope.

13. The kit of claim 11, wherein the working channel extension is flexible and capable of angular adjustment.

14. The kit of claim 13, wherein the working channel extension is configured for angular adjustment by actuation of the endoscope.

15. The kit of claim 13, wherein the coupler device further comprises an actuator for articulating the working channel extension.

16. The kit of claim 11, wherein the light and the camera lens provide a view in at least one direction substantially parallel to the longitudinal axis of the endoscope.

17. The kit of claim 11, wherein the main body of the coupler device comprises a distal end portion having an open area substantially aligned with a view provided by the light and the camera lens of the endoscope.

18. The kit of claim 11, wherein the working channel extension extends substantially parallel with the longitudinal axis of the endoscope, the working channel extension being configured for lateral angular adjustment to one or more orientations transverse to the longitudinal axis.

19. The kit of claim 11, further comprising an endoscopic device configured for advancement through the working channel of the endoscope and the working channel extension of the coupler device.

* * * * *